United States Patent
Mao et al.

(10) Patent No.: US 6,322,797 B1
(45) Date of Patent: *Nov. 27, 2001

(54) BIODEGRADABLE TEREPHTHALATE POLYESTER-POLY (PHOSPHATE) POLYMERS, COMPOSITIONS, ARTICLES, AND METHODS FOR MAKING AND USING THE SAME

(75) Inventors: Hai-Quan Mao, Towson; Kam W. Leong, Ellicott City; Wenbin Dang, Baltimore, all of MD (US); Hungnan Lo, Shaker Heights, OH (US); Zhong Zhao, Baltimore; David P. Nowotnik, Kingsville, both of MD (US); James P. English, Chelsea, AL (US)

(73) Assignees: Guilford Pharmaceuticals, Inc.; Johns Hopkins University, both of Baltimore, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/053,648

(22) Filed: Apr. 2, 1998

Related U.S. Application Data

(63) Continuation-in-part of application No. 08/832,215, filed on Apr. 3, 1997, now abandoned.

(51) Int. Cl.[7] ................................................... C08G 79/02
(52) U.S. Cl. .......................... 424/271; 528/398; 606/278; 523/115; 442/248; 428/378
(58) Field of Search ...................... 508/400, 398; 606/228; 523/115; 442/248; 428/378; 424/426; 528/400, 398

(56) References Cited

U.S. PATENT DOCUMENTS 2,891,915    6/1959   McCormack et al. .
(List continued on next page.)

FOREIGN PATENT DOCUMENTS 597473    5/1960   (CA) .
(List continued on next page.)

OTHER PUBLICATIONS

The claims of application No. 08/832215.*
(List continued on next page.)

Primary Examiner—Duc Truong
(74) Attorney, Agent, or Firm—Foley, Hoag & Eliot LLP

(57) ABSTRACT

Biodegradable terephthalate polymers are described comprising the recurring monomeric units shown in formula I:

$$\left[\left(O-R-O-\overset{O}{\underset{\|}{C}}-\text{C}_6\text{H}_4-\overset{O}{\underset{\|}{C}}-O-R-O-\underset{\underset{O-R'}{|}}{\overset{O}{\underset{\|}{P}}}\right)_x\left(O-R-O-\overset{O}{\underset{\|}{C}}-\text{C}_6\text{H}_4-\overset{O}{\underset{\|}{C}}\right)_2\right]_n$$

wherein R is a divalent organic moiety;
R' is an aliphatic, aromatic or heterocyclic residue;
x is ≧1; and
n is 0–5,000,
wherein the biodegradable polymer is biocompatible before and upon biodegradation.

Processes for preparing the polymers, compositions containing the polymers and biologically active substances, articles useful for implantation or injection into the body fabricated from the compositions, and methods for controllably releasing biologically active substances using the polymers, are also described.

126 Claims, 15 Drawing Sheets

U.S. PATENT DOCUMENTS

| | | |
|---|---|---|
| 3,271,329 | 9/1966 | Coover et al. |
| 3,442,982 | 5/1969 | Friedman |
| 3,927,231 | 12/1975 | Desitter et al. |
| 3,932,566 | 1/1976 | Reader |
| 4,100,354 | 7/1978 | Owen |
| 4,259,222 | 3/1981 | Login et al. |
| 4,328,174 | 5/1982 | Schmidt et al. |
| 4,474,937 | 10/1984 | Bales |
| 4,481,353 | 11/1984 | Nyilas et al. |
| 4,757,128 | 7/1988 | Domb et al. |
| 4,789,724 | 12/1988 | Domb et al. |
| 4,792,599 | 12/1988 | Durrani |
| 4,978,332 | 12/1990 | Luck et al. |
| 5,194,581 | 3/1993 | Leong |
| 5,213,804 | 5/1993 | Martin et al. |
| 5,256,765 | 10/1993 | Leong |
| 5,304,377 | 4/1994 | Yamada et al. |
| 5,530,093 | 6/1996 | Engelhardt et al. |
| 5,626,862 | 5/1997 | Brem et al. |
| 5,952,451 | 9/1999 | Zhao |

FOREIGN PATENT DOCUMENTS

| | | |
|---|---|---|
| 2250981 | 10/1997 | (CA) |
| 057116 | 8/1981 | (EP) |
| 0 193 019 | 9/1986 | (EP) |
| 0 386 757 | 9/1990 | (EP) |
| WO 95/17901 | 7/1995 | (WO) |
| WO 97/40085 | 10/1997 | (WO) |
| WO 98/58012 | 12/1998 | (WO) |

OTHER PUBLICATIONS

Pretula, "High–molecular–weight Poly (alkylene phosphonate) s by Condensation of Dialkylphosphonates with Diols", *Die Makromolekulare Chemie*, 191:3, 671–80 (1990).

Heller et al., "Release of Norethindrone from Poly (Ortho Esters)", *Polymer Engineering Sci.*, 21: 11, 727–31 (1981).

Wang, Ya Min, et al., In vitro and in vivo evaluation of taxol release from poly(lactic–co–glycolic acid) microspheres containing isopropyl myristate and degradation of the microspheres, *Journal of Controlled Release*, 49 (1997) 157–166.

Demetrick, Jeffrey S., et al., The Development of a Novel Intraperitoneal Tumor–Seeding Prophylactic, *The American Journal of Surgery®*, vol. 173, May 1997.

Francis, Prudence, et al., Phase I Feasibility and Pharmacologic Study of Weekly Intraperitoneal Paclitaxel: A Gynecologic Oncolgy Group Pilot Study, *Journal of Clinical Oncology*, vol. 13, No. 12 (Dec.), 1995: pp. 2961–2967.

Hagiwara, Akeo, M.D., et al., Pharmacologic Effects of Cisplatin Microspheres on Peritoneal Carcinomatosis in Rodents, *Cancer*, Feb. 1, 1993, vol. 71, No. 3, pp. 844–850.

Hagiwara, Akeo, et al., Clinical trials with intraperitoneal cisplatin microspheres for malignant ascites—a pilot study, *Anti–Cancer Drug Design* (1993), 8, 463–470.

Höckel, M. et al., Prevention of Peritoneal Adhesions in the Rat with Sustained Intraperitoneal Dexamethasone Delivered by a Novel Therapeutic System, *Annales Chirugiae et Gynaecologia* 76: 306–313, 1987.

Jameela, S.R., et al., Antitumour Activity of Mitoxantrone-–loaded Chitosan Microspheres Against Ehrlich Ascites Carcinoma, *J. Pharm. Pharmacol.* 1996, 48: 685–688.

Kumagai, Seisuke, et al., Improvement of Intraperitoneal Chemotherapy for Rat Ovarian Cancer Using Cisplatin— containing Microspheres, *Jpn. J. Cancer Res.* 87, 412–417, Apr. 1996.

Kadiyala, Sudha, et al., Poly(phosphoesters): Synthesis, Physico–Chemical Characterization and Biological Response in *Biomedical Applications of Synthetic Biodegradable Polymers*, Chapter 3 (Jeffrey O. Hollinger, ed. 1995).

Owusu–Ababio, G., et al., Efficacy of sustained release ciprofloxacin microspheres against device–associated *Pseudomonas aeruginosa* biofilm infection in a rabbit peritoneal model, J. Med. Microbiol., vol. 43 (1995), 368–376.

Pec, E.A., et al., Biological Activity of Urease Formulated in Poloxamer 407 after Intraperitoneal Injection in the Rat, *Journal of Pharmaceutical Sciences*, vol. 81, No. 7, Jul. 1992.

Sharma, Amarnath, et al., Antitumor Efficacy of Taxane Lipsomes on a Human Ovarian Tumor Xenograft in Nude Athymic Mice, *Journal of Pharmaceutical Sciences*, vol. 84, No. 12, Dec. 1995.

Kaetsu, Isao, et al., Biodegradable Implant Composites for Local Therapy, *Journal of Controlled Release*, 6 (1987) 249–263.

Zhang, Xichen, et al., Development of Biodegradable Polymeric Paste Formulations for Taxol: An In Vitro and In Vivo Study, *International Journal of Pharmaceutics* 137 (1996) 199–208.

Auerbach, Robert, et al., Site–Specific Drug Delivery to the Lung, *Polymers for Advanced Technologies*, vol. 3, pp. 323–329.

Walter, Kevin A., et al., Intratumoral Chemotherapy, *Neurosurgery*, vol. 37, No. 6, pp. 1129–1145, Dec. 1995.

Burt, Helen M., et al., Controlled Delivery of Taxol from Microspheres Composed of a Blend of Ethylene–Vinyl Acetate Copolymer and Poly (d,l–lactic acid), *Cancer Letters*, 88 (1995) 73–79.

Langer, Robert, New Methods of Drug Delivery, Science, 245; 1527–1533 (1990).

Leong, K.W., et al., Polymeric Controlled Drug Delivery, *Advanced Drug Delivery Reviews*, 1 (1987) 199–233.

Penczek, Stanislaw, et al., Phosphorus–Containing Polymers, In *Handbook of Polymer Synthesis*, Part B, Chapter 17, pp. 1077–1132 (Marcal Dekker, Inc.).

Bruin, P., et al., Biodegradable Lysine Diisocyanate–Based Poly(glycolide–co–e–caprolactone), *Biomaterials* 11(4): 291–5 (1990).

Pulapura, Satish, et al., Trends in the Development of Bioresorbable Polymers for Medical Applications, *Journal of Biomaterials Applications*, vol. 6, pp. 216–250, 1992.

Mao, Hai–Quan, et al., Synthesis and Biological Properties of Polymer Immunoadjuvants, *Polymer Journal*, vol. 25, No. 5, pp. 499–505 (1993).

Winternitz, Charles I., et al., Development of a Polymeric Surgical Paste Formulation for Taxol, *Pharmaceutical Research*, vol. 13, No. 3, pp. 368–375, 1996.

Wang, Ya Min, et al., Preparation and Characterization of Poly(lactic–co–glycolic acid) Microspheres for Targeted Delivery of a Novel Anticancer Agent, Taxol, *Chem. Pharm. Bull.* 44 (10) 1935–1940 (1996).

Sharma, Dayanand, Novel Taxol® Formulation: Polyvinylpyrrolidone Nanoparticle—Encapsulated Taxol® for Drug Delivery in Cancer Therapy, *Oncology Research,* vol. 8, Nos. 7/8, pp. 281–286, 1996.

Alkan–Onyuksel, Hayat, et al., A Mixed Micellar Formulation Suitable for the Parenteral Administration of Taxol, *Pharmaceutical Research,* vol. 11, No. 2, pp. 206–211, 1994.

Dordunoo, s.K., et al., Release of Taxol from Poly ($\epsilon$–caprolactone) Pastes: Effect of Water–Soluble Additives, *Journal of Controlled Release,* 44 (1997) 87–94.

Suh, Hearan, et al., Regulation of Smooth Muscle Cell Proliferation Using Paclitaxel–Loaded Poly(ethylene oxide-)–poly(lactide/glycolide) Nanospheres, *J. Biomed. Mater. Res.* 42(2): 331–8 (1998).

Lo, Hungnan, Synthesis of Biodegradable Polymers and Porous Grafts for Orthopedic Applications, *Thesis,* Johns Hopkins University, 1995.

Chemical Abstracts, vol. 99, No. 22, abstract No. 176481 Akutin et al. Polyarylates (1983).

* cited by examiner

FIG. 2A

80/20-B, DMSO
OBSERVE H1
   FREQUENCY 399.952 MHz
   SPECTRAL WIDTH 5000.0 Hz
   ACQUISITION TIME 3.744 sec
   RELAXATION DELAY 0.000 sec
   PULSE WIDTH 7.0μsec
   AMBIENT TEMPERATURE
   NO. REPETITIONS 12
DOUBLE PRECISION ACQUISITION
DATA PROCESSING
   FT SIZE 65536
TOTAL ACQUISITION TIME 1 minute

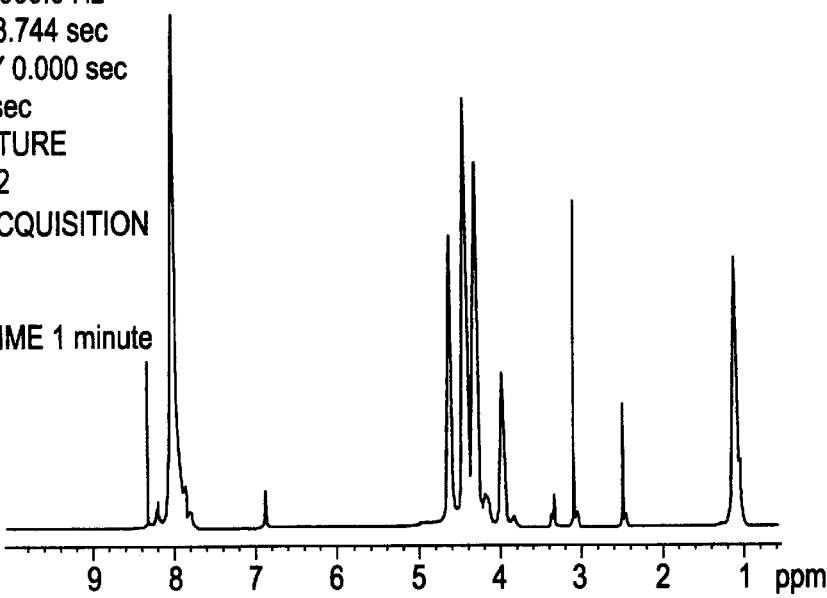

FIG. 2B

80/20-B,BB, DMSO
OBSERVE P31
   FREQUENCY 161.903 MHz
   SPECTRAL WIDTH 16000.0 Hz
   ACQUISITION TIME 0.800 sec
   RELAXATION DELAY 0.000 sec
   PULSE WIDTH 10.0μsec
   TEMPERATURE 37.0°C
   NO. REPETITIONS 77
DECOUPLE H1
   HIGH POWER 33
   DECOUPLER CONTINUOUSLY ON
   WALTZ16 MODULATED
DOUBLE PRECISION ACQUISITION
DATA PROCESSING
   LINE BROADENING 15.0Hz
   FT SIZE 32768
TOTAL ACQUISITION TIME 1 minute

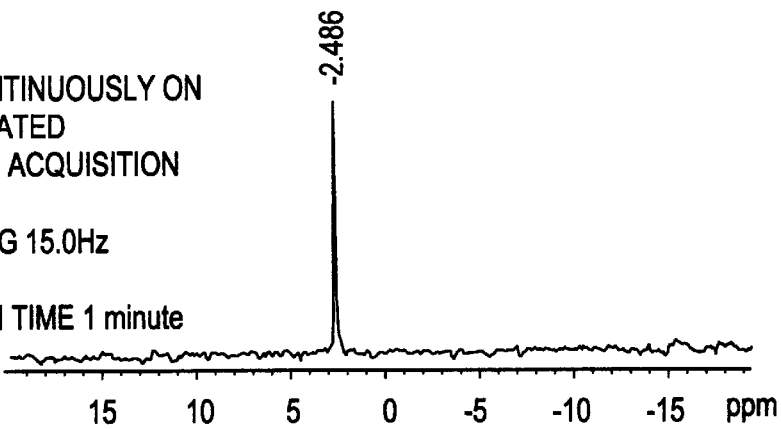

| Polymer | Mn (VPO) | Mw/Mn (GPC) | Elemental Analysis; Found (Theory) | | |
|---|---|---|---|---|---|
| | | | C (%) | H (%) | P (%) |
| P(BHET-EOP/TC, 80/20) | 7918 | 6119 /2219 | 49.61 (51.82) | 4.95 (4.81) | 6.24 (7.03) |
| P(BHET-HOP/TC, 90/10) | 6364 | 4201 /1587 | 51.67 (53.11) | 5.99 (5.90) | 6.26 (6.77) |

—○— PLGA (RG755)

—●— P(BHET-EOP/TC, 80/20)

BIODEGRADABLE TEREPHTHALATE POLYESTER-POLY (PHOSPHATE) POLYMERS, COMPOSITIONS, ARTICLES, AND METHODS FOR MAKING AND USING THE SAME

This application is a continuation-in-part application of U.S. patent application Ser. No. 08/832,215, filed Apr. 3. 1997, now incomplete application, the contents of which are incorporated herein in their entirety.

BACKGROUND OF THE INVENTION

1. Field of the Invention

The present invention relates to biodegradable homopolymer and block copolymer compositions, in particular those containing both phosphate and terephthalate ester linkages in the polymer backbone, which degrade in vivo into non-toxic residues. The polymers of the invention are particularly useful as implantable medical devices and drug delivery systems.

2. Description of the Prior Art

Biocompatible polymeric materials have been used extensively in therapeutic drug delivery and medical implant device applications. Sometimes, it is also desirable for such polymers to be, not only biocompatible, but also biodegradable to obviate the need for removing the polymer once its therapeutic value has been exhausted.

Conventional methods of drug delivery, such as frequent periodic dosing, are not ideal in many cases. For example, with highly toxic drugs, frequent conventional dosing can result in high initial drug levels at the time of dosing, often at near-toxic levels, followed by low drug levels between doses that can be below the level of their therapeutic value. However, with controlled drug delivery, drug levels can be more easily maintained at therapeutic, but non-toxic, levels by controlled release in a predictable manner over a longer term.

If a biodegradable medical device is intended for use as a drug delivery or other controlled-release system, using a polymeric carrier is one effective means to deliver the therapeutic agent locally and in a controlled fashion, see Langer et al., "Chemical and Physical Structures of Polymers as Carriers for Controlled Release of Bioactive Agents", *J. Macro. Science, Rev. Macro. Chem. Phys.,* C23:1, 61–126 (1983). As a result, less total drug is required, and toxic side effects can be minimized. Polymers have been used as carriers of therapeutic agents to effect a localized and sustained release. See Leong et al., "Polymeric Controlled Drug Delivery", *Advanced Drug Delivery Reviews,* 1:199–233 (1987); Langer, "New Methods of Drug Delivery", *Science,* 249:1527–33 (1990); and Chien et al., *Novel Drug Delivery Systems* (1982). Such delivery systems offer the potential of enhanced therapeutic efficacy and reduced overall toxicity.

For a non-biodegradable matrix, the steps leading to release of the therapeutic agent are water diffusion into the matrix, dissolution of the therapeutic agent, and diffusion of the therapeutic agent out through the channels of the matrix. As a consequence, the mean residence time of the therapeutic agent existing in the soluble state is longer for a non-biodegradable matrix than for a biodegradable matrix, for which passage through the channels of the matrix, while it may occur, is no longer required. Since many pharmaceuticals have short half-lives, therapeutic agents can decompose or become inactivated within the non-biodegradable matrix before they are released. This issue is particularly significant for many bio-macromolecules and smaller polypeptides, since these molecules are generally hydrolytically unstable and have low permeability through a polymer matrix. In fact, in a non-biodegradable matrix, many bio-macromolecules aggregate and precipitate, blocking the channels necessary for diffusion out of the carrier matrix.

These problems are alleviated by using a biodegradable matrix that, in addition to some diffusion release, also allows controlled release of the therapeutic agent by degradation of the polymer matrix. Examples of classes of synthetic polymers that have been studied as possible biodegradable materials include polyesters (Pitt et al., "Biodegradable Drug Delivery Systems Based on Aliphatic Polyesters: Application to contraceptives and Narcotic Antagonists", *Controlled Release of Bioactive Materials,* 19–44 (Richard Baker ed., 1980); poly(amino acids) and pseudo-poly(amino acids) (Pulapura et al., "Trends in the Development of Bioresorbable Polymers for Medical Applications", *J. of Biomaterials Appl.,* 6:1, 216–50 (1992); polyurethanes (Bruin et al., "Biodegradable Lysine Diisocyanate-based Poly(Glycolide-co-ε Caprolactone)-Urethane Network in Artificial Skin", *Biomaterials,* 11:4, 291–95 (1990); poly-orthoesters (Heller et al., "Release of Norethindrone from Poly(Ortho Esters)", *Polymer Engineering Sci.,* 21:11, 727–31 (1981); and polyanhydrides (Leong et al., "Polyanhydrides for Controlled Release of Bioactive Agents", *Biomaterials* 7:5, 364–71 (1986). Specific examples of biodegradable materials that are used as medical implant materials are polylactide, polyglycolide, polydioxanone, poly(lactide-co-glycolide), poly(glycolide-co-polydioxanone), polyanhydrides, poly(glycolide-co-trimethylene carbonate), and poly(glycolide-co-caprolactone).

Polymers having phosphate linkages, called poly (phosphates), poly(phosphonates) and poly(phosphites), are known. See Penczek et al., *Handbook of Polymer Synthesis,* Chapter 17: "Phosphorus-Containing Polymers", (Hans R. Kricheldorf ed., 1992). The respective structures of these three classes of compounds, each having a different side chain connected to the phosphorus atom, is as follows:

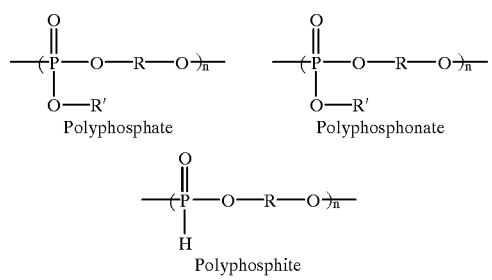

The versatility of these polymers comes from the versatility of the phosphorus atom, which is known for a multiplicity of reactions. Its bonding can involve the 3p orbitals or various 3s–3p hybrids; spd hybrids are also possible because of the accessible d orbitals. Thus, the physico-chemical properties of the poly(phosphoesters) can be readily changed by varying either the R or R' group. The biodegradability of the polymer is due primarily to the physiologically labile phosphoester bond in the backbone of the polymer. By manipulating the backbone or the sidechain, a wide range of biodegradation rates are attainable.

An additional feature of poly(phosphoesters) is the availability of functional side groups. Because phosphorus can be pentavalent, drug molecules or other biologically active substances can be chemically linked to the polymer. For example, drugs with -O-carboxy groups may be coupled to the phosphorus via an ester bond, which is hydrolyzable. The P—O—C group in the backbone also lowers the glass transition temperature of the polymer and, importantly, confers solubility in common organic solvents, which is desirable for easy characterization and processing.

Login et al., in U.S. Pat. Nos. 4,259,222; 4,315,847; and 4,315,969, disclose a poly(phosphate)-polyester polymer having a halogenated terephthalate recurring unit useful in flame retardant materials, but without a phosphorus having a side chain.

Kadiyala et al., *Biomedical Applications of Synthetic Biodegradable Polymers,* Chapter 3: "Poly(phosphoesters): Synthesis, Physicochemical Characterization and Biological Response", 33–57 (Jeffrey O. Hollinger ed., 1995) at page 40 discloses the synthesis of bis(2-hydroxyethyl) terephthalate (BHET) and its subsequent reaction with dimethyl phosphite to form the corresponding poly(phosphite):

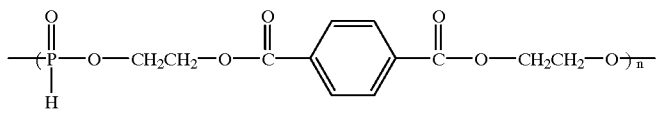

A number of other patents disclose flame retardants having a polyester-linked terephthalate recurring unit and may also have a poly(phosphonate) recurring unit having a —P—R' side chain in which an R' group has replaced the hydrogen atom of a poly(phosphite), but lacking the intervening oxygen of a poly(phosphate). See, for example, Desitter et al., U.S. Pat. No. 3,927,231 and Reader, U.S. Pat. No. 3,932,566. Starck et al., U.S. Pat. No. 597,473 disclose side chains that can be substituted with many kinds of groups including an alkoxy group, but the document as a whole makes it clear that poly(phosphonates), rather than poly(phosphates), are contemplated. (See column 2, lines 28–40.)

Engelhardt et al., U.S. Pat. No. 5,530,093 discloses a multitude of textile finishing compositions having a wide variety of polycondensate structures with phosphoester recurring units, including some with terephthalate recurring units, but no guidance is provided to indicate that poly (phosphates), rather than the other two classes of phosphoester polymers, should be selected for making biodegradable materials.

Thus, there remains a need for materials such as the terephthalate polyester-poly(phosphate) polymers of the invention, which are particularly well-suited for making biodegradable materials and other biomedical applications.

SUMMARY OF THE INVENTION

The biodegradable terephthalate polymers of the invention comprise the recurring monomeric units shown in formula I:

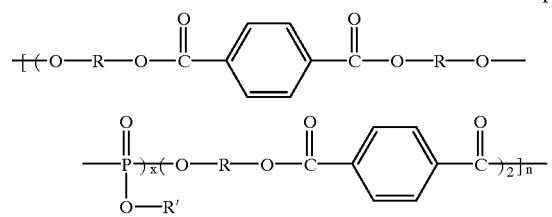

wherein R is a divalent organic moiety;
R' is an aliphatic, aromatic or heterocyclic residue;
x is $\geq 1$; and
n is 0–5,000,
where the biodegradable polymer is sufficiently pure to be biocompatible and degrades to biocompatible residues upon biodegradation.

In another embodiment, the invention contemplates a process for preparing a biodegradable terephthalate homopolymer comprising the step of polymerizing p moles of a diol compound having formula II:

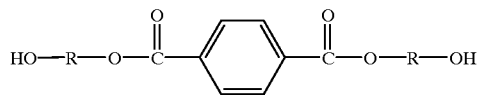

wherein R is as defined above, with q moles of a phosphorodichloridate of formula III:

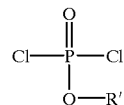

wherein R' is defined as above, and p>q, to form q moles of a homopolymer of formula IV, shown below:

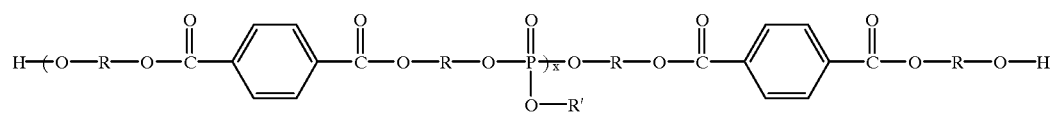

wherein R, R' and x are as defined above.

The invention also contemplates a process for preparing a biodegradable block copolymer comprising the steps of:
(a) the polymerization step discribed above; and
(b) further reacting the homopolymer of formula IV and excess diol of formula II with (p−q) moles of terephthaloyl chloride having the formula V:

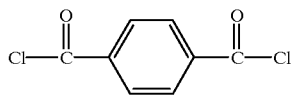

to form a block copolymer of formula I.

In another embodiment, the invention comprises a biodegradable terephthalate polymer composition comprising:
(a) at least one biologically active substance and
(b) a polymer having the recurring monomeric units shown in formula I.

In yet another embodiment of the invention, an article useful for implantation, injection, or otherwise being placed totally or partially within the body, comprises the biodegradable terephthalate polymer of formula I or the above-described polymer composition.

In yet another embodiment of the invention, a method is provided for the controlled release of a biologically active substance comprising the steps of:
(a) combining the biologically active substance with a biodegradable terephthalate polymer having the recurring monomeric units shown in formula I to form an admixture;
(b) forming the admixture into a shaped, solid article; and
(c) implanting or injecting the solid article in vivo at a preselected site, such that the solid implanted or injected article is in at least partial contact with a biological fluid.

BRIEF DESCRIPTION OF THE DRAWINGS

FIG. 2A shows the $^1$H-NMR spectrum, and FIG. 2B shows the $^{31}$P-NMR spectrum for P(BHET-EOP/TC, 80/20).

DETAILED DESCRIPTION OF THE INVENTION

Polymers of the Invention

Figure 1A:
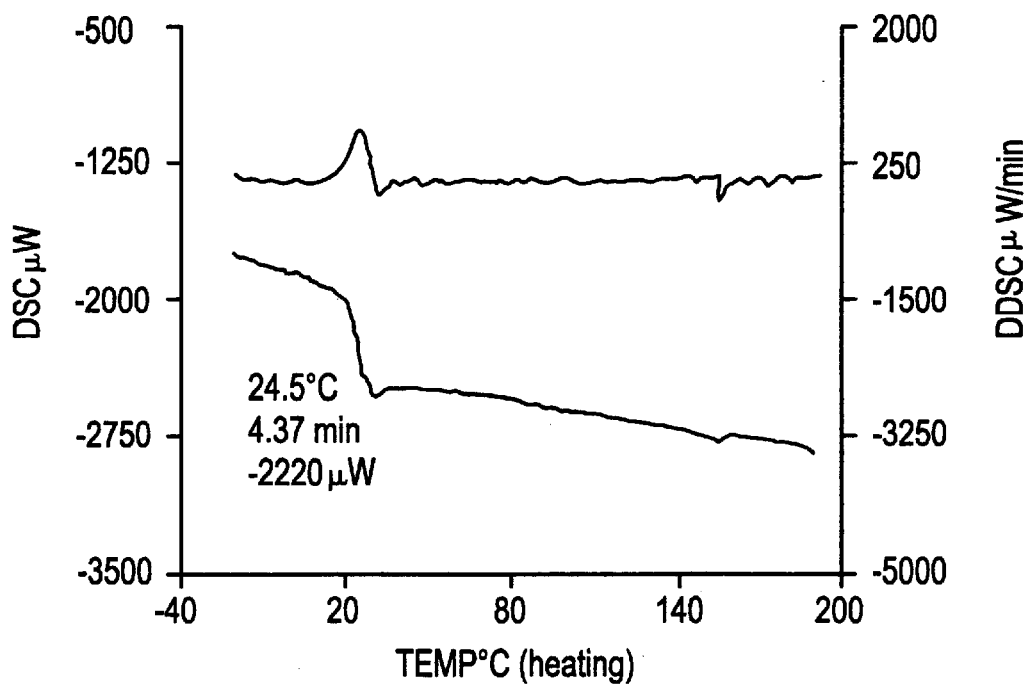
FIG. 1A shows the DSC curve of P(BHET-EOP/TC, 80/20)

As used herein, the term "aliphatic" refers to a linear, branched, or cyclic alkane, alkene, or alkyne. Preferred aliphatic groups in the poly(phosphate) polymer of the invention are linear or branched alkane having from 1 to 10 carbons, preferably being linear alkane groups of 1 to 7 carbon atoms.

As used herein, the term "aromatic" refers to an unsaturated cyclic carbon compound with $4n+2\pi$ electrons.

As used herein, the term "heterocyclic" refers to a saturated or unsaturated ring compound having one or more atoms other than carbon in the ring, for example, nitrogen, oxygen or sulfur.

The biodegradable terephthalate polymer of the invention comprises the recurring monomeric units shown in formula I:

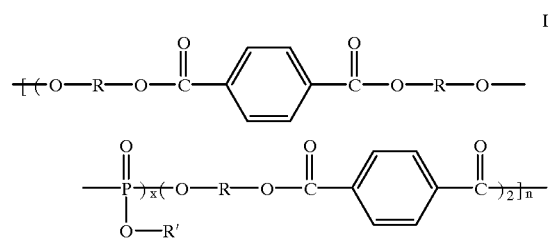

wherein R is a divalent organic moiety. R can be any divalent organic moiety so long as it does not interfere with the polymerization, copolymerization, or biodegradation reactions of the polymer. Specifically, R can be an aliphatic group, for example, alkylene, such as ethylene, 1,2-dimethylethylene, n-propylene, isopropylene, 2-methylpropylene, 2,2'-dimethyl-propylene or tert-butylene, tert-pentylene, n-hexylene, n-heptylene and the like; alkenylene, such as ethenylene, propenylene, dodecenylene, and the like; alkynylene, such as propynylene, hexynylene, octadecenynylene, and the like; an aliphatic group substituted with a non-interfering substituent, for example, hydroxy-, halogen- or nitrogen-substituted aliphatic group; or a cycloaliphatic group such as cyclopentylene, 2-methylcyclopentylene, cyclohexylene, cyclohexenylene and the like.

R can also be a divalent aromatic group, such as phenylene, benzylene, naphthalene, phenanthrenylene, and the like, or a divalent aromatic group substituted with a non-interfering substituent. Further, R can be a divalent heterocyclic group, such as pyrrolylene, furanylene, thiophenylene, alkylene-pyrrolylene-alkylene, pyridylene, pyridinylene, pyrimidinylene and the like, or may be any of these substituted with a non-interfering substituent.

Preferably, however, R is an alkylene group, a cycloaliphatic group, a phenylene group, or a divalent group having the formula:

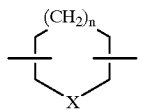

wherein X is oxygen, nitrogen, or sulfur, and n is 1 to 3. More preferably, R is an alkylene group having from 1 to 7 carbon atoms and, most preferably, R is an ethylene group, a 2-methyl-propylene group, or a 2,2'-dimethylpropylene group.

R' in the polymer of the invention is an aliphatic, aromatic or heterocyclic residue. When R' is aliphatic, it is preferably alkyl, such as methyl, ethyl, n-propyl, isopropyl, n-butyl, tert-butyl, —$C_8H_{17}$, and the like; alkyl substituted with a non-interfering substituent, such as halogen, alkoxy or nitro; or alkyl conjugated to a biologically active substance to form a pendant drug delivery system. When R' is aromatic, it typically contains from about 5 to about 14 carbon atoms, preferably about 5 to 12 carbon atoms and, optionally, can contain one or more rings that are fused to each other. Examples of particularly suitable aromatic groups include phenyl, naphthyl, anthracenyl, phenanthrenyl and the like.

When R' is heterocyclic, it typically contains from about 5 to 14 ring atoms, preferably from about 5 to 12 ring atoms, and one or more heteroatoms. Examples of suitable heterocyclic groups include furan, thiophene, pyrrole, isopyrrole, 3-isopyrrole, pyrazole, 2-isoimidazole, 1,2,3-triazole, 1,2,4-triazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-dioxazol. 1,2,4-dioxazole, 1,3,2-dioxazole, 1,3,4-dioxazole, 1,2,5-oxatriazole, 1,3-oxathiole, 1,2-pyran, 1,4-pyran, 1,2-pyrone, 1,4-pyrone, 1,2-dioxin, 1,3-dioxin, pyridine, N-alkyl pyridinium, pyridazine, pyrimidine, pyrazine, 1,3,5-triazine, 1,2,4-triazine, 1,2,3-triazine, 1,2,4-oxazine, 1,3,2-oxazine, 1,3,5-oxazine, 1,4-oxazine, o-isoxazine, p-isoxazine, 1,2,5-oxathiazine, 1,2,6-oxathiazine, 1,4,2-oxadiazine, 1,3,5,2-oxadiazine, azepine, oxepin, thiepin, 1,2,4-diazepine, indene, isoindene, benzofuran, isobenzofuran, thionaphthene, isothionaphthene, indole, indolenine, 2-isobenzazole, 1,4-pyrindine, pyrando[3,4-b]-pyrrole, isoindazole, indoxazole, benzoxazole, anthranil, 1,2-benzopyran, 1,2-benzopyrone, 1,4-benzopyrone, 2,1-benzopyrone, 2,3-benzopyrone, quinoline, isoquinoline, 12,-benzodiazine, 1,3-benzodiazine, naphthyridine, pyrido[3,4-b]-pyridine, pyrido[3,2-b]-pyridine, pyrido[4,3-b] pyridine, 1,3,2-benzoxazine, 1,4,2-benzoxazine, 2,3,1-benzoxazine, 3,1,4-benzoxazine, 1,2-benzisoxazine, 1,4-benzisoxazine, carbazole, xanthrene, acridine, purine, and the like. Preferably, when R' is heterocyclic, it is selected from the group consisting of furan, pyridine, N-alkylpyridine, 1,2,3- and 1,2,4-triazoles, indene, anthracene and purine.

In a particularly preferred embodiment, R' is an alkyl group or a phenyl group and, even more preferably, an alkyl group having from 1 to 7 carbon atoms. Most preferably, RI is an ethyl group.

The value of x can vary greatly depending on the desired solubility of the polymer, the desired Tg, the desired stability of the polymer, the desired stiffness of the final polymers, and the biodegradability and the release characteristics desired in the polymer. However, x generally is $\geq 1$ and, typically, varies between about 1 and 40. Preferably, x is from about 1 to about 30, more preferably, from about 1 to about 20 and, most preferably, from about 2 to about 20.

The most common way of controlling the value of x is to vary the feed ratio of the "x" portion relative to the other monomer. For example, in the case of making the polymer:

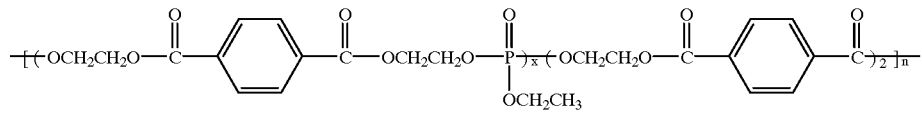

widely varying feed ratios of the ethyl phosphorodichloridate "x" reactant ("EOP") can be used with the terephthaloyl chloride reactant ("TC"). Feed ratios of EOP to TC can easily vary from 99:1 to 1:99, for example, 95:5, 90:10, 85:15, 80:20, 75:25, 70:30, 65:35, 60:40, 55:45, 50:50, 45:55, 20:80, 15:85, and the like. Preferably, the EOP/TC feed ratio varies from about 90:10 to about 50:50; even more preferably, from about 85:15 to about 50:50; and, most preferably from about 80:20 to about 50:50.

The number n can vary greatly depending on the biodegradability and the release characteristics desired in the polymer, but typically varies between about 0 to 5,000, preferably between about 2 and 500. More preferably, n is from about 5 to about 300 and, most preferably, from about 5 to about 200.

Biodegradable polymers differ from non-biodegradable polymers in that they can be degraded during in vivo therapy. This generally involves breaking down the polymer into its monomeric subunits. In principle, the ultimate hydrolytic breakdown products of a poly(phosphate) are phosphate, alcohol, and diol, all of which are potentially non-toxic. The intermediate oligomeric products of the hydrolysis may have different properties, but the toxicology of a biodegradable polymer intended for implantation or injection, even one synthesized from apparently innocuous monomeric structures, is typically determined after one or more in vitro toxicity analyses.

The biodegradable polymer of the invention is preferably sufficiently pure to be biocompatible itself and remains biocompatible upon biodegradation. By "biocompatible" is meant that the biodegradation products or the polymer are non-toxic and result in only minimal tissue irritation when implanted or injected into vasculated tissue.

The polymer of the invention is preferably soluble in one or more common organic solvents for ease of fabrication and processing. Common organic solvents include such solvents as chloroform, dichloromethane, acetone, ethyl acetate, DMAC, N-methyl pyrrolidone, dimethylformamide, and dimethylsulfoxide. The polymer is preferably soluble in at least one of the above solvents.

The glass transition temperature (Tg) of the polymer of the invention can vary widely depending upon the degree of branching of the diols used to prepare the polymer, the relative proportion of phosphorous-containing monomer used to make the polymer, and the like. However, preferably, the Tg is within the range of from about −10° C. to about 80° C. and, even more preferably, between about 0 and 50° C.

Synthesis of Polyester-Poly(phosphate) Polymers

The most common general reaction in preparing poly(phosphates) is a dehydrochlorination between a phosphorodichloridate and a diol according to the following equation:

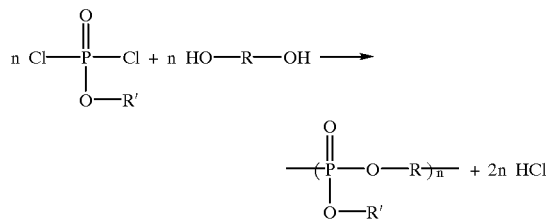

A Friedel-Crafts reaction can also be used to synthesize poly(phosphates). Polymerization typically is effected by reacting either bis(chloromethyl) compounds with aromatic hydrocarbons or chloromethylated diphenyl ether with triaryl phosphates. Poly(phosphates) can also be obtained by bulk condensation between phosphorus diimidazolides and aromatic diols, such as resorcinol and quinoline, usually under nitrogen or some other inert gas.

An advantage of bulk polycondensation is that it avoids the use of solvents and large amounts of other additives, thus making purification more straightforward. It can also provide polymers of reasonably high molecular weight. Somewhat rigorous conditions, however, are often required and can lead to chain acidolysis (or hydrolysis if water is present). Unwanted, thermally-induced side reactions, such as cross-linking reactions, can also occur if the polymer backbone is susceptible to hydrogen atom abstraction or oxidation with subsequent macroradical recombination. To minimize these side reactions, the polymerization is preferably carried out in solution.

Solution polycondensation requires that both the diol and the phosphorus component be soluble in a common solvent. Typically, a chlorinated organic solvent is used, such as chloroform, dichloromethane, or dichloroethane. The solution polymerization is preferably run in the presence of equimolar amounts of the reactants and a stoichiometric amount of an acid acceptor, usually a tertiary amine such as pyridine or triethylamine. The product is then typically isolated from the solution by precipitation with a nonsolvent and purified to remove the hydrochloride salt by conventional techniques known to those of ordinary skill in the art, such as by washing with an aqueous acidic solution, e.g., dilute HCl.

Reaction times tend to be longer with solution polymerization than with bulk polymerization. However, because overall milder reaction conditions can be used, side reactions are minimized, and more sensitive functional groups can be incorporated into the polymer. The disadvantages of solution polymerization are that the attainment of high molecular weights, such as a Mw greater than 20,000, is less likely.

Interfacial polycondensation can be used when high molecular weight polymers are desired at high reaction rates. Mild conditions minimize side reactions. Also the dependence of high molecular weight on stoichiometric equivalence between diol and dichloridate inherent in solution methods is removed. However, hydrolysis of the acid chloride may occur in the alkaline aqueous phase. Sensitive dichloridates that have some solubility in water are generally subject to hydrolysis rather than polymerization. Phase transfer catalysts, such as crown ethers or tertiary ammonium chloride, can be used to bring the ionized diol to the interface to facilitate the polycondensation reaction. The yield and molecular weight of the resulting polymer after interfacial polycondensation are affected by reaction time, molar ratio of the monomers, volume ratio of the immiscible solvents, the type of acid acceptor, and the type and concentration of the phase transfer catalyst.

In a preferred embodiment of the invention, the process of making a biodegradable terephthalate homopolymer of formula I comprises the step of polymerizing p moles of a diol compound having formula II:

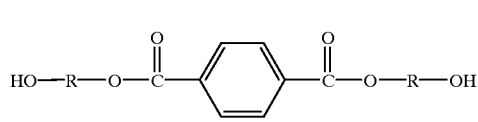

wherein R is as defined above, with q moles of a phosphorodichloridate of formula III:

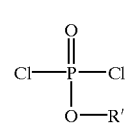

wherein R' is defined as above, and p>q, to form q moles of a homopolymer of formula IV, shown below:

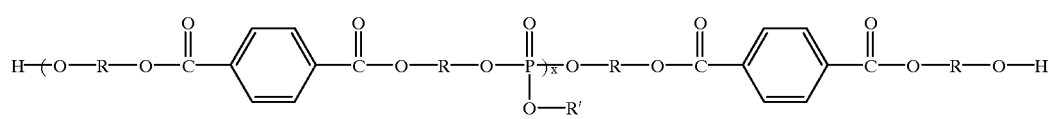

wherein R, R' and x are as defined above. The homopolymer so formed can be isolated, purified and used as is. Alternatively, the homopolymer, isolated or not, can be used to prepare a block copolymer of the invention by:

(a) polymerizing as described above; and (b) further reacting the homopolymer of formula IV and excess diol of formula II with (p−q) moles of terephthaloyl chloride having the formula V:

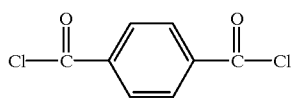

to form the polymer of formula I.

The function of the polymerization reaction of step (a) is to phosphorylate the di-ester starting material and then to polymerize it to form the homopolymer. The polymerization step (a) can take place at widely varying temperatures, depending upon the solvent used, the molecular weight desired, the solubility desired, and the susceptibility of the reactants to form side reactions. Preferably, however, the polymerization step (a) takes place at a temperature from about −40 to about +160° C. for solution polymerization, preferably from about 0 to 65° C.; in bulk, temperatures in the range of about +150° C. are generally used.

The time required for the polymerization step (a) also can vary widely, depending on the type of polymerization being used and the molecular weight desired. Preferably, however, the polymerization step (a) takes place during a time between about 30 minutes and 24 hours.

While the polymerization step (a) may be in bulk, in solution, by interfacial polycondensation, or any other convenient method of polymerization, preferably, the polymerization step (a) is a solution polymerization reaction. Particularly when solution polymerization reaction is used, an acid acceptor is advantageously present during the polymerization step (a). A particularly suitable class of acid acceptor comprises tertiary amines, such as pyridine, trimethylamine, triethylamine, substituted anilines and substituted aminopyridines. The most preferred acid acceptor is the substituted aminopyridine 4-dimethylaminopyridine ("DMAP").

The addition sequence for the polymerization step (a) can vary significantly depending upon the relative reactivities of the diol of formula II, the phosphorodichloridate of formula III, and the homopolymer of formula IV; the purity of these reactants; the temperature at which the polymerization reaction is performed; the degree of agitation used in the polymerization reaction; and the like. Preferably, however, the diol of formula II is combined with a solvent and an acid acceptor, and then the phosphorodichloridate is added slowly. For example, a solution of the phosphorodichloridate in a solvent may be trickled in or added dropwise to the chilled reaction mixture of diol, solvent and acid acceptor, to control the rate of the polymerization reaction.

The purpose of the copolymerization of step (b) is to form a block copolymer comprising (i) the phosphorylated homopolymer chains produced as a result of polymerization step (a) and (ii) interconnecting polyester units. The result is a block copolymer having a microcrystalline structure particularly well-suited to use as a controlled release medium.

The copolymerization step (b) of the invention usually takes place at a slightly higher temperature than the temperature of the polymerization step (a), but also may vary widely, depending upon the type of copolymerization reaction used, the presence of one or more catalysts, the molecular weight desired, the solubility desired, and the susceptibility of the reactants to undesirable side reaction. However, when the copolymerization step (b) is carried out as a solution polymerization reaction, it typically takes place at a temperature between about −40 and 100° C. Typical solvents include methylene chloride, chloroform, or any of a wide variety of inert organic solvents.

The time required for the copolymerization of step (b) can also vary widely, depending on the molecular weight of the material desired and, in general, the need to use more or less rigorous conditions for the reaction to proceed to the desired degree of completion. Typically, however, the copolymerization step (b) takes place during a time of about 30 minutes to 24 hours.

The addition sequence for the copolymerization step (b) can vary significantly depending upon the relative reactivities of the homopolymer of formula IV and the terephthaloyl chloride of formula V; the purity of these reactants; the temperature at which the copolymerization reaction is performed; the degree of agitation used in the copolymerization reaction; and the like. Preferably, however, the terephthaloyl chloride of formula V is added slowly to the reaction mixture, rather than vice versa. For example, a solution of the terephthaloyl chloride in a solvent may be trickled in or added dropwise to the chilled or room temperature reaction, to control the rate of the copolymerization reaction.

The polymer of formula I, whether a homopolymer (where y is 0) or a block copolymer (where Y is greater than 0), is isolated from the reaction mixture by conventional techniques, such as by precipitating out, extraction with an immiscible solvent, evaporation, filtration, crystallization and the like. Typically, however, the polymer of formula I is both isolated and purified by quenching a solution of said polymer with a non-solvent or a partial solvent, such as diethyl ether or petroleum ether.

When the polymer of the invention is synthesized by a two-step solution polycondensation to produce a block copolymer, the addition sequence of the reactive chlorides and the reaction temperatures in each step are preferably optimized to obtain the combination of molecular weight desired with good solubility in common organic solvents. Preferably, the additive sequence comprises dissolving the bis-terephthalate starting material with an acid acceptor in a solvent in which both are soluble, chilling the solution with stirring, slowly adding an equal molar amount of the phosphorodichloridate (dissolved in the same solvent) to the solution, allowing the reaction to proceed at room temperature for a period of time, slowly adding an appropriate amount of terephthaloyl chloride, which is also dissolved in the same solvent, and increasing the temperature to about 50° C. before refluxing overnight.

Biodegradability and Release Characteristics

The polymer of formula I is usually characterized by a release rate of the biologically active substance in vivo that is controlled, at least in part, as a function of hydrolysis of the phosphoester bond of the polymer during biodegradation. Additionally, the biologically active substance to be released may be conjugated to the phosphorus side chain R' to form a pendant drug delivery system.

Further, the structure of the side chain can influence the release behavior of the polymer. For example, it is expected that conversion of the phosphorous side chain to a more lipophilic, more hydrophobic or bulky group would slow down the degradation process. Thus, for example, release is usually faster from polymer compositions with a small aliphatic group side chain than with a bulky aromatic side chain.

The lifetime of a biodegradable polymer in vivo also depends upon its molecular weight, crystallinity, biostability, and the degree of cross-linking. In general, the greater the molecular weight, the higher the degree of crystallinity, and the greater the biostability, the slower biodegradation will be. Accordingly, degradation times can vary widely, preferably from less than a day to several months.

Polymer Compositions

The polymer of formula I can be used either alone or as a composition containing, in addition, a biologically active substance to form a variety of useful biodegradable materials. For example, the polymer of formula I can be used to produce a biosorbable suture, an orthopedic appliance or bone cement for repairing injuries to bone or connective tissue, a laminate for degradable or non-degradable fabrics, or a coating for an implantable device, even without the presence of a biologically active substance.

Preferably, however, the biodegradable terephthalate polymer composition comprises both:
(a) at least one biologically active substance and
(b) the polymer having the recurring monomeric units shown in formula I where R, R', and x and n are as defined above.

The biologically active substance of the invention can vary widely with the purpose for the composition. The active substance(s) may be described as a single entity or a combination of entities. The delivery system is designed to be used with biologically active substances having high water-solubility as well as with those having low water-solubility to produce a delivery system that has controlled release rates. The term "biologically active substance" includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Non-limiting examples of broad categories of useful biologically active substances include the following therapeutic categories: anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and antithyroid agents, uterine relaxants, vitamins, and prodrugs.

More specifically, non-limiting examples of useful biologically active substances include the following therapeutic categories: analgesics, such as nonsteroidal anti-inflammatory drugs, opiate agonists and salicylates; antihistamines, such as $H_1$-blockers and $H_2$-blockers; anti-infective agents, such as anthelmintics, antianaerobics, antibiotics, aminoglycoside antibiotics, antifungal antibiotics, cephalosporin antibiotics, macrolide antibiotics, miscellaneous β-lactam antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, antiretroviral agents, scabicides, and urinary anti-infectives; antineoplastic agents, such as alkylating agents, nitrogen mustard aklylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics; autonomic agents, such as anticholinergics, antimuscarinic anticholinergics, ergot alkaloids, parasympathomimetics, cholinergic agonist parasympathomimetics, cholinesterase inhibitor parasympathomimetics, sympatholytics, α-blocker sympatholytics, β-blocker sympatholytics, sympathomimetics, and adrenergic agonist sympathomimetics; cardiovascular agents, such as antianginals, β-blocker antianginals, calcium-channel blocker antianginals, nitrate antianginals, antiarrhythmics, cardiac glycoside antiarrhythmics, class I antiarrhythmics, class II antiarrhythmics, class III antiarrhythmics, class IV antiarrhythmics, antihypertensive agents, α-blocker antihypertensives, angiotensin-converting enzyme inhibitor (ACE inhibitor) antihypertensives, β-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, HMG-COA reductase inhibitor antilipemics, inotropes, cardiac glycoside inotropes, and thrombolytic agents; dermatological agents, such as antihistamines, anti-inflammatory agents, corticosteroid anti-inflammatory agents, antipruritics/local anesthetics, topical anti-infectives, antifungal topical anti-infectives, antiviral topical anti-infectives, and topical antineoplastics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, $H_2$-blocker anti-ulcer agents, cholelitholytic agents, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hematological agents, such as antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, such as abortifacients, adrenal agents, corticosteroid adrenal agents, androgens, anti-androgens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immunosuppressive anti-inflammatory agents, nonsteroidal anti-inflammatory drugs (NSAIDs), salicylate anti-inflammatory agents, skeletal muscle relaxants, neuromuscular blocker skeletal muscle relaxants, and reverse neuromuscular blocker skeletal muscle relaxants; neurological agents, such as anticonvulsants, barbiturate anticonvulsants, benzodiazepine anticonvulsants, anti-migraine agents, antiparkinsonian agents, anti-vertigo agents, opiate agonists, and opiate antagonists; ophthalmic agents, such as antiglaucoma agents, β-blocker anti-gluacoma agents, miotic anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid anti-inflammatory agents, and ophthalmic nonsteroidal anti-inflammatory drugs (NSAIDs); psychotropic agents, such as antidepressants, heterocyclic antidepressants, monoamine oxidase inhibitors (MAOIs), selective serotonin re-uptake inhibitors (SSRIs), tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory anti-inflammatory agents, and respiratory corticosteroid anti-inflammatory agents; toxicology agents, such as antidotes, heavy metal antagonists/chelating agents, substance abuse agents, deterrent substance abuse agents, and withdrawal substance abuse agents; minerals; and vitamins, such as vitamin A, vitamin B, vitamin C, vitamin D, vitamin E, and vitamin K.

Preferred classes of useful biologically active substances from the above categories include: (1) nonsteroidal anti-inflammatory drugs (NSAIDs) analgesics, such as diclofenac, ibuprofen, ketoprofen, and naproxen; (2) opiate agonist analgesics, such as codeine, fentanyl, hydromorphone, and morphine; (3) salicylate analgesics, such as aspirin (ASA) (enteric coated ASA); (4) Hl-blocker antihistamines, such as clemastine and terfenadine; (5) $H_2$-blocker antihistamines, such as cimetidine, famotidine, nizadine, and ranitidine; (6) anti-infective agents, such as mupirocin; (7) antianaerobic anti-infectives, such as chloramphenicol and clindamycin; (8) antifungal antibiotic anti-infectives, such as amphotericin b, clotrimazole, fluconazole, and ketoconazole; (9) macrolide antibiotic anti-infectives, such as azithromycin and erythromycin; (10) miscellaneous β-lactam antibiotic anti-infectives, such as aztreonam and imipenem; (11) penicillin antibiotic anti-infectives, such as nafcillin, oxacillin, penicillin G, and penicillin V; (12) quinolone antibiotic anti-infectives, such as ciprofloxacin and norfloxacin; (13) tetracycline antibiotic anti-infectives, such as doxycycline, minocycline, and tetracycline; (14) antituberculosis antimycobacterial anti-infectives such as isoniazid (INH), and rifampin; (15) antiprotozoal anti-infectives, such as atovaquone and dapsone; (16) antimalarial antiprotozoal anti-infectives, such as chloroquine and pyrimethamine; (17) anti-retroviral anti-infectives, such as ritonavir and zidovudine; (18) antiviral anti-infective agents, such as acyclovir, ganciclovir, interferon alfa, and rimantadine; (19) alkylating antineoplastic agents, such as carboplatin and cisplatin; (20) nitrosourea alkylating antineoplastic agents, such as carmustine (BCNU); (21) antimetabolite antineoplastic agents, such as methotrexate; (22) pyrimidine analog antimetabolite antineoplastic agents, such as fluorouracil (5-FU) and gemcitabine; (23) hormonal antineoplastics, such as goserelin, leuprolide, and tamoxifen; (24) natural antineoplastics, such as aldesleukin, interleukin-2, docetaxel, etoposide (VP-16), interferon alfa, paclitaxel, and tretinoin (ATRA); (25) antibiotic natural antineoplastics, such as bleomycin, dactinomycin, daunorubicin, doxorubicin, and mitomycin; (26) vinca alkaloid natural antineoplastics, such as vinblastine and vincristine; (27) autonomic agents, such as nicotine; (28) anticholinergic autonomic agents, such as benztropine and trihexyphenidyl; (29) antimuscarinic anticholinergic autonomic agents, such as atropine and oxybutynin; (30) ergot alkaloid autonomic agents, such as bromocriptine; (31) cholinergic agonist parasympathomimetics, such as pilocarpine; (32) cholinesterase inhibitor parasympathomimetics, such as pyridostigmine; (33) α-blocker sympatholytics, such as prazosin; (34) 9-blocker sympatholytics, such as atenolol; (35) adrenergic agonist sympathomimetics, such as albuterol and dobutamine; (36) cardiovascular agents, such as aspirin (ASA) (enteric coated ASA); (37) i-blocker antianginals, such as atenolol and propranolol; (38) calcium-channel blocker antianginals, such as nifedipine and verapamil; (39) nitrate antianginals, such as isosorbide dinitrate (ISDN); (40) cardiac glycoside antiarrhythmics, such as digoxin; (41) class I antiarrhythmics, such as lidocaine, mexiletine, phenytoin, procainamide, and quinidine; (42) class II antiarrhythmics, such as atenolol, metoprolol, propranolol, and timolol; (43) class III antiarrhythmics, such as amiodarone; (44) class IV antiarrhythmics, such as diltiazem and verapamil; (45) α-blocker antihypertensives, such as prazosin; (46) angiotensin-converting enzyme inhibitor (ACE inhibitor) antihypertensives, such as captopril and enalapril; (47) β-blocker antihypertensives, such as atenolol, metoprolol, nadolol, and propranolol; (48) calcium-channel blocker antihypertensive agents, such as diltiazem and nifedipine; (49) central-acting adrenergic antihypertensives, such as clonidine and methyldopa; (50) diurectic antihypertensive agents, such as amiloride, furosemide, hydrochlorothiazide (HCTZ), and spironolactone; (51) peripheral vasodilator antihypertensives, such as hydralazine and minoxidil; (52) antilipemics, such as gemfibrozil and probucol; (53) bile acid sequestrant antilipemics, such as cholestyramine; (54) HMG-CoA reductase inhibitor antilipemics, such as lovastatin and pravastatin; (55) inotropes, such as amrinone, dobutamine, and dopamine; (56) cardiac glycoside inotropes, such as digoxin; (57) thrombolytic agents, such as alteplase (TPA), anistreplase, streptokinase, and urokinase; (58) dermatological agents, such as colchicine, isotretinoin, methotrexate, minoxidil, tretinoin (ATRA); (59) dermatological corticosteroid anti-inflammatory agents, such as betamethasone and dexamethasone; (60) antifungal topical anti-infectives, such as amphotericin B, clotrimazole, miconazole, and nystatin; (61) antiviral topical anti-infectives, such as acyclovir; (62) topical antineoplastics, such as fluorouracil (5-FU); (63) electrolytic and renal agents, such as lactulose; (64) loop diuretics, such as furosemide; (65) potassium-sparing diuretics, such as triamterene; (66) thiazide diuretics, such as hydrochlorothiazide (HCTZ); (67) uricosuric agents, such as probenecid; (68) enzymes such as RNase and DNase; (69) thrombolytic enzymes, such as alteplase, anistreplase, streptokinase and urokinase; (70) antiemetics, such as prochlorperazine; (71) salicylate gastrointestinal anti-inflammatory agents, such as sulfasalazine; (72) gastric acid-pump inhibitor anti-ulcer agents, such as omeprazole; (73) $H_2$-blocker anti-ulcer agents, such as cimetidine, famotidine, nizatidine, and ranitidine; (74) digestants, such as pancrelipase; (75) prokinetic agents, such as erythromycin; (76) opiate agonist intravenous anesthetics such as fentanyl; (77) hematopoietic anti-anemia agents, such as erythropoietin, filgrastim (G-CSF), and sargramostim (GM-CSF); (78) coagulation agents, such as antihemophilic factors 1–10 (AHF 1–10); (79) anticoagulants, such as warfarin; (80) thrombolytic enzyme coagulation agents, such as alteplase, anistreplase, streptokinase and urokinase; (81) hormones and hormone modifiers, such as bromocriptine; (82) abortifacients, such as methotrexate; (83) antidiabetic agents, such as insulin; (84) oral contraceptives, such as estrogen and progestin; (85) progestin contraceptives, such as levonorgestrel and norgestrel; (86) estrogens such as conjugated estrogens, diethylstilbestrol (DES), estrogen (estradiol, estrone, and estropipate); (87) fertility agents, such as clomiphene, human chorionic gonadatropin (HCG), and menotropins; (88) parathyroid agents such as calcitonin; (89) pituitary hormones, such as desmopressin, goserelin, oxytocin, and vasopressin (ADH); (90) progestins, such as medroxyprogesterone, norethindrone, and progesterone; (91) thyroid hormones, such as levothyroxine; (92) immunobiologic agents, such as interferon beta-lb and interferon gamma-lb; (93) immunoglobulins, such as immune globulin IM, IMIG, IGIM and immune globulin IV, IVIG, IGIV; (94) amide local anesthetics, such as lidocaine; (95) ester local anesthetics, such as benzocaine and procaine; (96) musculoskeletal corticosteroid anti-inflammatory agents, such as beclomethasone, betamethasone, cortisone, dexamethasone, hydrocortisone, and prednisone; (97) musculoskeletal anti-inflammatory immunosuppressives, such as azathioprine, cyclophosphamide, and methotrexate; (98) musculoskeletal nonsteroidal anti-inflammatory drugs (NSAIDs), such as diclofenac, ibuprofen, ketoprofen, ketorlac, and naproxen; (99) skeletal muscle relaxants, such as baclofen, cyclobenzaprine, and diazepam; (100) reverse neuromuscular blocker skeletal muscle relaxants, such as pyridostigmine; (101) neurological agents, such as nimodipine, riluzole, tacrine and ticlopidine; (102) anticonvulsants, such as carbamazepine, gabapentin, lamotrigine, phenytoin, and valproic acid; (103) barbiturate anticonvulsants, such as phenobarbital and primidone; (104) benzodiazepine anticonvulsants, such as clonazepam, diazepam, and lorazepam; (105) anti-parkisonian agents, such as bromocriptine, levodopa, carbidopa, and pergolide; (106) anti-vertigo agents, such as meclizine; (107) opiate agonists, such as codeine, fentanyl, hydromorphone, methadone, and morphine; (108) opiate antagonists, such as naloxone; (109) β-blocker anti-glaucoma agents, such as timolol; (110) miotic anti-glaucoma agents, such as pilocarpine; (111) ophthalmic aminoglycoside antiinfectives, such as gentamicin, neomycin, and tobramycin; (112) ophthalmic quinolone anti-infectives, such as ciprofloxacin, norfloxacin, and ofloxacin; (113) ophthalmic corticosteroid anti-inflammatory agents, such as dexamethasone and prednisolone; (114) ophthalmic nonsteroidal anti-inflammatory drugs (NSAIDs), such as diclofenac; (115) antipsychotics, such as clozapine, haloperidol, and risperidone; (116) benzodiazepine anxiolytics, sedatives and hypnotics, such as clonazepam, diazepam, lorazepam, oxazepam, and prazepam; (117) psychostimulants, such as methylphenidate and pemoline; (118) antitussives, such as codeine; (119) bronchodilators, such as theophylline; (120) adrenergic agonist bronchodilators, such as albuterol; (121) respiratory corticosteroid anti-inflammatory agents, such as dexamethasone; (122) antidotes, such as flumazenil and naloxone; (123) heavy metal antagonists/chelating agents, such as penicillamine; (124) deterrent substance abuse agents, such as disulfiram, naltrexone, and nicotine; (125) withdrawal substance abuse agents, such as bromocriptine; (126) minerals, such as iron, calcium, and magnesium; (127) vitamin B compounds, such as cyanocobalamin (vitamin $B_{12}$) and niacin (vitamin $B_3$); (128) vitamin C compounds, such as ascorbic acid; and (129) vitamin D compounds, such as calcitriol.

In addition to the foregoing, the following less common drugs may also be used: chlorhexidine; estradiol cypionate in oil; estradiol valerate in oil; flurbiprofen; flurbiprofen sodium; ivermectin; levodopa; nafarelin; and somatropin.

Further, the following new drugs may also be used: recombinant bovine beta-glucan; bovine immunoglobulin concentrate; bovine superoxide dismutase; the formulation comprising fluorouracil, epinephrine, and bovine collagen; recombinant hirudin (r-Hir), HIV-1 immunogen; human anti-TAC antibody; recombinant human growth hormone (r-hGH); recombinant human hemoglobin (r-Hb); recombinant human mecasermin (r-IGF-1); recombinant interferon beta-la; lenograstim (G-CSF); olanzapine; recombinant thyroid stimulating hormone (r-TSH); and topotecan.

Further still, the following intravenous products may be used: acyclovir sodium; aldesleukin; atenolol; bleomycin sulfate, human calcitonin; salmon calcitonin; carboplatin; carmustine; dactinomycin, daunorubicin HCl; docetaxel; doxorubicin HCl; epoetin alfa; etoposide (VP-16); fluorouracil (5-FU); ganciclovir sodium; gentamicin sulfate; interferon alfa; leuprolide acetate; meperidine HCl; methadone HCl; methotrexate sodium; paclitaxel; ranitidine HCl; vinblastin sulfate; and zidovudine (AZT).

Further specific examples of useful biologically active substances from the above categories include: (a) antineoplastics such as androgen inhibitors, antimetabolites, cytotoxic agents, and immunomodulators; (b) anti-tussives such as dextromethorphan, dextromethorphan hydrobromide, noscapine, carbetapentane citrate, and chlorphedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, codeine sulfate and morphine; (f) mineral supplements such as potassium chloride, zinc chloride, calcium carbonates, magnesium oxide, and other alkali metal and alkaline earth metal salts; (g) ion exchange resins such as cholestryramine; (h) anti-arrhythmics such as N-acetylprocainamide; (i) antipyretics and analgesics such as acetaminophen, aspirin and ibuprofen; (j) appetite suppressants such as phenyl-propanolamine hydrochloride or caffeine; (k) expectorants such as guaifenesin; (1) antacids such as aluminum hydroxide and magnesium hydroxide; (m) biologicals such as peptides, polypeptides, proteins and amino acids, hormones, interferons or cytokines, and other bioactive peptidic compounds, such as interleukins 1–18 including mutants and analogues, RNase, DNase, luteinizing hormone releasing hormone (LHRH) and analogues, gonadotropin releasing hormone (GnRH), transforming growth factor-β (TGF-β), fibroblast growth factor (FGF), tumor necrosis factor-α & β (TNF-α& β), nerve growth factor (NGF), growth hormone releasing factor (GHRF), epidermal growth factor (EGF), fibroblast growth factor homologous factor (FGFHF), hepatocyte growth factor (HGF), insulin growth factor (IGF), invasion inhibiting factor-2 (IIF-2), bone morphogenetic proteins 1–7 (BMP 1–7), somatostatin, thymosin-α-1, T-globulin, superoxide dismutase (SOD), complement factors, hGH, tPA, calcitonin, ANF, EPO and insulin; and (n) anti-infective agents such as antifungals, anti-virals, antiseptics and antibiotics.

Alternatively, the biologically active substance may be a radiosensitizer, such as metoclopramide, sensamide or neusensamide (manufactured by Oxigene); profiromycin (made by Vion); RSR13 (made by Allos); Thymitaq (made by Agouron), etanidazole or lobenguane (manufactured by Nycomed); gadolinium texaphrin (made by Pharmacyclics); BuDR/Broxine (made by NeoPharm); IPdR (made by Sparta); CR2412 (made by Cell Therapeutic); L1X (made by Terrapin); or the like.

Preferably, the biologically active substance is selected from the group consisting of peptides, poly-peptides, proteins, amino acids, polysaccharides, growth factors, hormones, anti-angiogenesis factors, interferons or cytokines, and pro-drugs. In a particularly preferred embodiment, the biologically active substance is a therapeutic drug or pro-drug, most preferably a drug selected from the group consisting of chemotherapeutic agents and other anti-neoplastics such as paclitaxel, antibiotics, antivirals, antifungals, anti-inflammatories, and anticoagulants.

The biologically active substances are used in amounts that are therapeutically effective. While the effective amount of a biologically active substance will depend on the particular material being used, amounts of the biologically active substance from about 1% to about 65% have been easily incorporated into the present delivery systems while achieving controlled release. Lesser amounts may be used to achieve efficacious levels of treatment for certain biologically active substances.

Pharmaceutically acceptable carriers may be prepared from a wide range of materials. Without being limited thereto, such materials include diluents, binders and adhesives, lubricants, disintegrants, colorants, bulking agents, flavorings, sweeteners and miscellaneous materials such as buffers and adsorbents in order to prepare a particular medicated composition.

Implants and Delivery Systems Designed for Injection

In its simplest form, a biodegradable therapeutic agent delivery system consists of a dispersion of the therapeutic agent in a polymer matrix. The therapeutic agent is typically released as the polymeric matrix biodegrades in vivo into soluble products that can be absorbed by and eventually excreted from the body.

In a particularly preferred embodiment, an article is used for implantation, injection, or otherwise placed totally or partially within the body, the article comprising the biodegradable terephthalate polymer composition of the invention. The biologically active substance of the composition and the polymer of the invention may form a homogeneous matrix, or the biologically active substance may be encapsulated in some way within the polymer. For example, the biologically active substance may be first encapsulated in a microsphere and then combined with the polymer in such a way that at least a portion of the microsphere structure is maintained.

Alternatively, the biologically active substance may be sufficiently immiscible in the polymer of the invention that it is dispersed as small droplets, rather than being dissolved, in the polymer. Either form is acceptable, but it is preferred that, regardless of the homogeneity of the composition, the release rate of the biologically active substance in vivo remain controlled, at least partially as a function of hydrolysis of the phosphoester bond of the polymer upon biodegradation.

In a preferred embodiment, the article of the invention is designed for implantation or injection into the body of an animal. It is particularly important that such an article result in minimal tissue irritation when implanted or injected into vasculated tissue.

As a structural medical device, the polymer compositions of the invention provide a physical form having specific chemical, physical, and mechanical properties sufficient for the application, in addition to being a composition that degrades in vivo into non-toxic residues. Typical structural medical articles include such implants as orthopedic fixation devices, ventricular shunts, laminates for degradable fabric, drug-carriers, biosorbable sutures, burn dressings, coatings to be placed on other implant devices, and the like.

In orthopedic articles, the composition of the invention may be useful for repairing bone and connective tissue injuries. For example, a biodegradable porous material can be loaded with bone morphogenetic proteins to form a bone graft useful for even large segmental defects. In vascular graft applications, a biodegradable material in the form of woven fabric can be used to promote tissue ingrowth. The polymer composition of the invention may be used as a temporary barrier for preventing tissue adhesion, e.g., following abdominal surgery.

On the other hand, in nerve regeneration articles, the presence of a biodegradable supporting matrix can be used to facilitate cell adhesion and proliferation. When the polymer composition is fabricated as a tube for nerve generation, for example, the tubular article can also serve as a geometric guide for axonal elongation in the direction of functional recovery.

As a drug delivery device, the polymer compositions of the invention provide a polymeric matrix capable of sequestering a biologically active substance and provide predictable, controlled delivery of the substance. The polymeric matrix then degrades to non-toxic residues.

Biodegradable medical implant devices and drug delivery products can be prepared in several ways. The polymer can be melt processed using conventional extrusion or injection molding techniques, or these products can be prepared by dissolving in an appropriate solvent, followed by formation of the device, and subsequent removal of the solvent by evaporation or extraction. By these methods, the polymers may be formed into drug delivery systems of almost any size or shape desired, for example, implantable solid discs or wafers or injectable rods, microspheres, or other microparticles.

Once a medical implant article is in place, it should remain in at least partial contact with a biological fluid, such as blood, internal organ secretions, mucous membranes, cerebrospinal fluid and the like.

The following examples are illustrative of preferred embodiments of the invention and are not to be construed as limiting the invention thereto. All polymer molecular weights are average molecular weights. All percentages are based on the percent by weight of the final delivery system or formulation being prepared, unless otherwise indicated, and all totals equal 100% by weight.

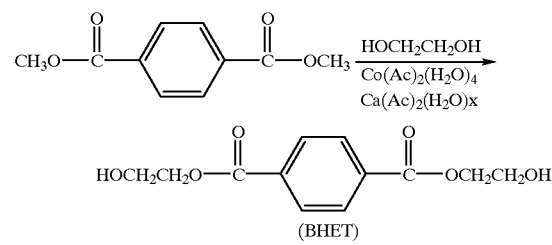

1.4 moles of dimethyl terephthalate (277 g) and 7.2 moles of ethylene glycol (445 g) were weighed into a one-liter liter round-bottomed flask connected to a vacuum line. A catalytic amount of cobalt (II) acetate tetrahydrate (180 mg, 0.5 mole) and calcium acetate hydrate (90 mg, 0.4 mole) were added. The reaction mixture was heated at 160° C. in an oil bath under a mild vacuum.

After 18 hours, the reaction was terminated. While still molten, the mixture was poured into cold water. The precipitate formed was collected, dried under vacuum, and redissolved into warm methanol. The sludge (composed largely of oligomers) was filtered off. The filtrate was cooled to −200C to form a precipitate, which was recrystallized in methanol and ethyl acetate to produce a white powder, the product "BHET".

Alternatively, BHET having excellent purity may be prepared according to the following reaction scheme:

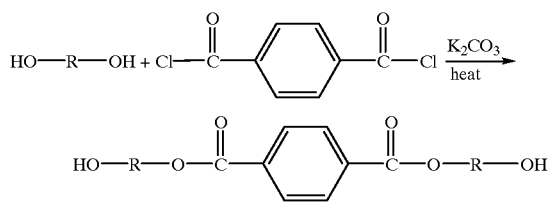

BHET is also commercially available.

lymerization of the homopolymer P(BHET-EOP) with the additional monomer TC to form the copolymer P(BHET-EOP/TC).

The solvent was then evaporated, and the residue was redissolved in about 100–200 mL of chloroform. The chloroform solution was washed with a saturated NaCl solution three times, dried over anhydrous $Na_2SO_4$, and quenched into ether. The resulting precipitate was redissolved in chloroform and quenched again into ether. The resulting tough, off-white solid precipitate was filtered off and dried under vacuum. Yield 82%.

Figure 3:
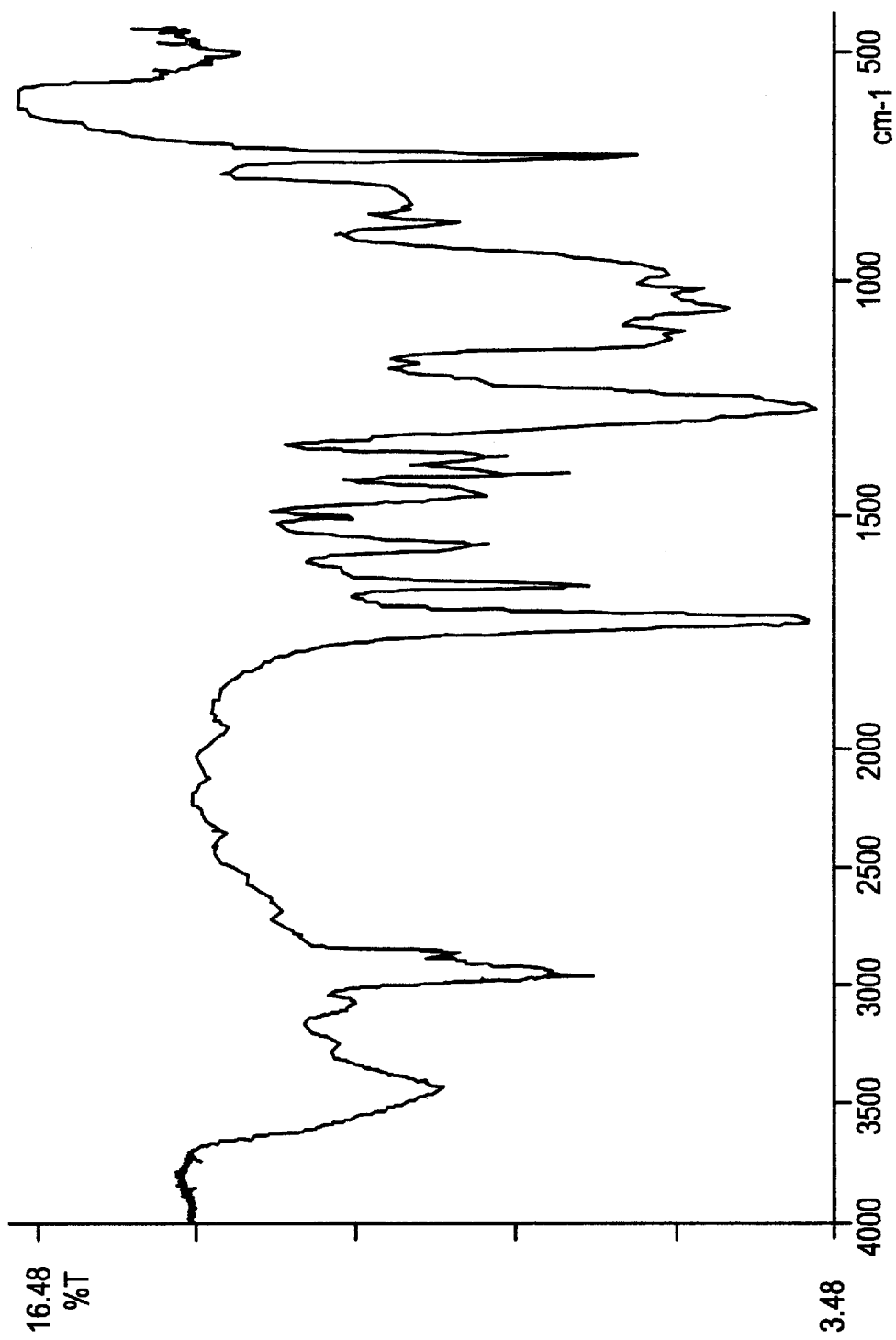
FIG. 3 shows the FT-IR spectrum for P(BHET-EOP/TC, 80/20).
Figures 4, 5:
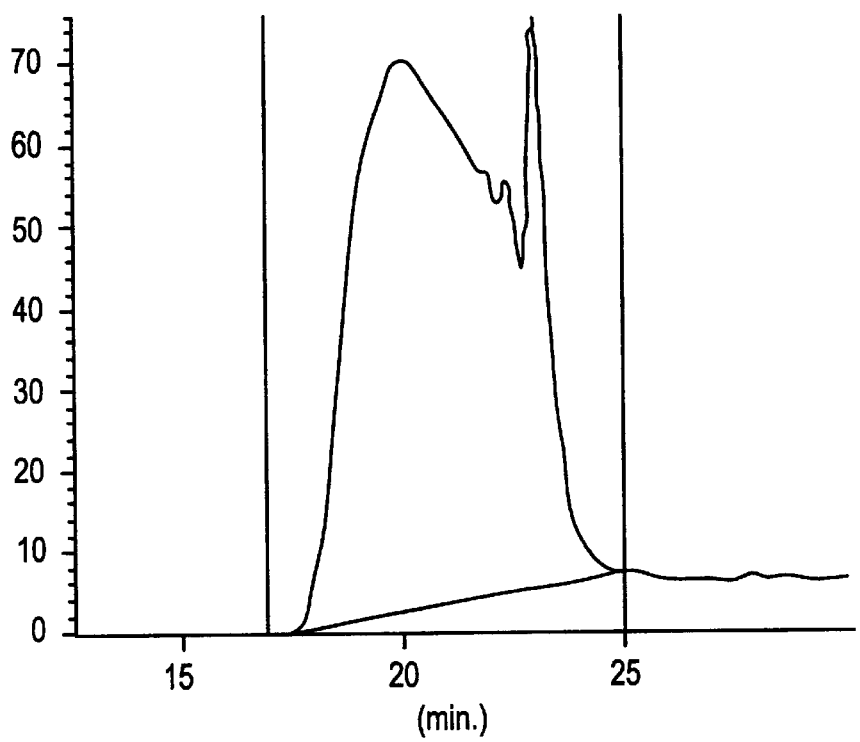
FIG. 4 shows the GPC chromatogram for P(BHET-EOP/TC, 80/20).
FIG. 5 shows the molecular weights and elemental analyses for P(BHET-EOP/TC, 80/20) and P(BHET-HOP/TC, 90/10).

The structure of P(BHET-EOP/TC, 80/20) was ascertained by $^1$H-NMR, $^{31}$P-NMR and FT-IR spectra, as shown in FIGS. 2 and 3. The structure was also confirmed by elemental analysis, which correlated closely with theoretical ratios. The results of the elemental analysis are shown in FIG. 5.

The molecular weight of P(BHET-EOP/TC, 80/20) was first measured by gel permeation chromatography (GPC) with polystyrene as the calibration standard. The resulting graph established a weight average molecular weight (Mw) of about 6100 and a number average molecular weight (Mn) of about 2200, as shown in FIG. 4. Vapor pressure osmometry ("VPO") for this copolymer gave an Mn value of about

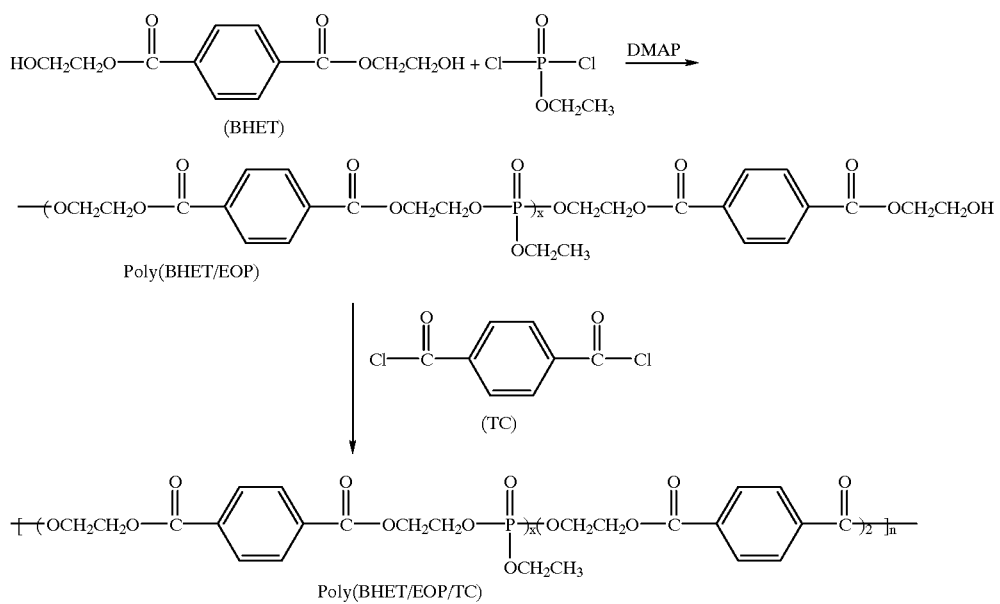

Under an argon stream, 10 g of 1,4-bis(hydroxyethyl) terephthalate (BHET) prepared as described above in Example 1, 9.61 g of 4-dimethylaminopyridine (DMAP), and 70 mL of methylene chloride were placed in a 250 mL flask equipped with a funnel. The solution in the flask was cooled down to −40° C. with stirring, and a solution of 5.13 g of ethyl phosphorodichloridate (EOP) (distilled before use) in 20 mL of methylene chloride was added dropwise through the funnel. After addition was complete, the mixture was stirred at room temperature for four hours to form the homopolymer BHET-EOP.

A solution of 1.60 g of terephthaloyl chloride (TC) (obtained from Aldrich Chemical Company and recrystallized with hexane before use) in 20 mL of methylene chloride was then added drop by drop. The temperature was brought up to about 45–50° C. gradually, and the reaction mixture was kept refluxing overnight to complete the copo- 7900. The results of these molecular weight studies are also shown in FIG. 5.

Example 3

Feed Ratio Variations of P(BHET-EOP/TC)

A series of other P(BHET-EOP/TC) copolymers of the invention were prepared by following the procedure described above in Example 2 except that the feed ratio of the EOP to TC used during the initial polymerization step and copolymerization step respectively was varied. The results are shown below in Table 1. From the feed ratio of EOP/TC, the value of "x" from the formula shown below can be calculated. For example, in P(BHET-EOP/TC, 80/20) prepared above in Example 2, x is 8.

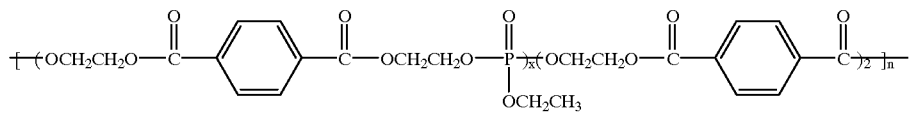

TABLE 1

Variation of Feed Ratio of EOP to TC in P(BHET-EOP/TC)

| Feed Ratio of EOP/TC* | 100/0 | 95/5 | 90/10 | 85/15 | 80/20 | 50:50 |
|---|---|---|---|---|---|---|
| "x" | — | 38 | 18 | 11.4 | 8 | 2 |

*Feed ratio of ethyl phosphorodichloridate to terephthaloyl chloride.

Example 4

Synthesis of Copolymers P(BHET-HOP/TC, 80:20 and 90:10)

The phosphoester copolymers P(BHET-HOP/TC, 80:20) and P(BHET-HOP/TC, 90:10) were prepared by the procedure described above in Example 2, except that hexyl phosphorodichloridate ("HOP") was substituted for the monomer ethyl phosphoro-dichloridate (EOP) during the initial polymerization step, and the feed ratio was varied.

For P(BHET-HOP/TC, 90:10), the elemental analysis, the Mw/Mn value as determined by GPC, and the Mn as determined by VPO, were all ascertained and are shown in FIG. 5.

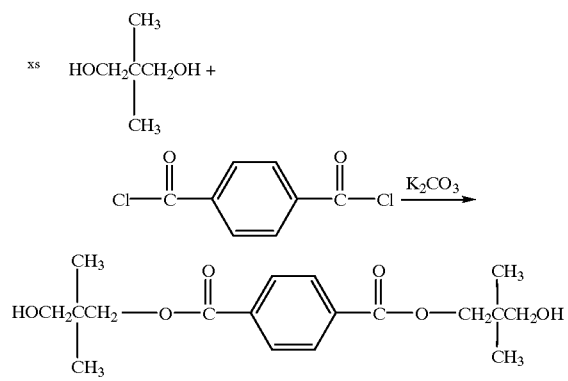

Bis(3-hydroxy-2,2'-dimethylpropyl)terephthalate (BHDPT) was synthesized by reacting terephthaloyl chloride (TC) with an excess of the diol 2,2'-dimethyl-1,3-propanediol in 2-butanone with $K_2CO_3$ as the acid acceptor.

Example 6

Synthesis and Isolation of the Homopolymer P (BHDPT-EOP)

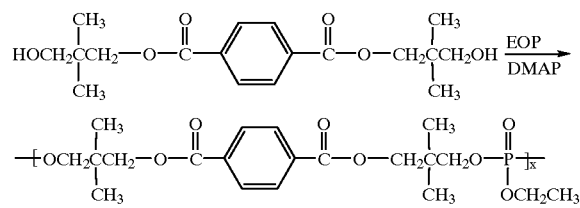

The BHDPT monomer prepared in Example 5 above and the acid acceptor 4-dimethylaminopyridine (DMAP) were dissolved in methylene chloride. The resulting solution was chilled to −70° C. using a dry ice/acetone bath, and an equal molar amount of ethyl phosphorodichloridate (EOP) was slowly added. The reaction mixture was then heated and refluxed overnight. The salt formed in the polymerization was removed by filtration. The remaining polymer solution (filtrate) was washed with a saturated NaCl solution three times, and the homopolymer was precipitated in diethyl ether.

Example 7

Synthesis of Copolymer P(BHDPT-EOP/TC)

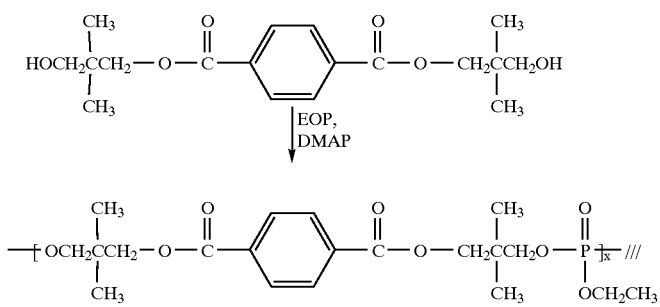

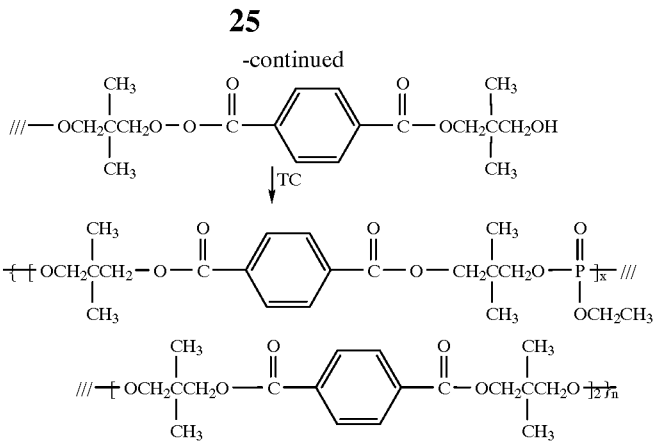

Copolymers of P(BHDPT-EOP) with TC were synthesized by the two-step solution copolymerization shown above. After the reaction between BHDPT and EOP had proceeded at room temperature for one hour, the reaction flask was cooled in a dry ice/acetone bath. An appropriate amount of TC (the number of moles of TC and EOP combined equaled the number of moles of BHDPT) was slowly added to the flask. The reaction mixture was then heated and refluxed overnight. The salt formed in the polymerization was removed by filtration. The remaining copolymer solution (filtrate) was washed with a saturated NaCl solution three times, and the copolymer was precipitated out in diethyl ether.

Example 8

Feed Ratio Variations for P(BHDPT-EOP/TC)

A series of other P(BHDPT-EOP/TC) copolymers of the invention were prepared by following the procedure described above in Example 7, except that the feed ratio of EOP to TC, which were used during the initial polymerization step and the copolymerization step respectively, were varied. The results are shown below in Table 2. From the feed ratio of EOP/TC, the value of x from the formula shown below can be calculated. For example, in P(BHDPT-EOP/TC, 80/20), the value of x is 8.

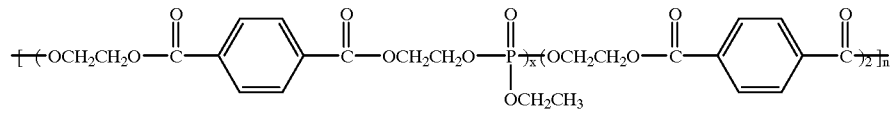

TABLE 2

Variation of Feed Ratio of EOP to TC in P(BHDPT-EOP/TC)

| Feed Ratio of EOP/TC* | 100/0 | 90/10 | 85/15 | 80/20 | 75/25 | 50:50 |
|---|---|---|---|---|---|---|
| "x" | — | 18 | 11.4 | 8 | 6 | 2 |

*Feed ratio of ethyl phosphorodichloridate to terephthaloyl chloride.

Example 9

Synthesis and Isolation of the Homopolymer P(BHDPT-HOP)

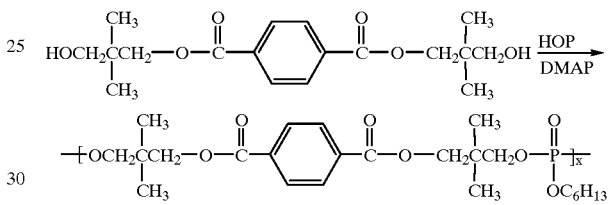

The BHDPT monomer prepared in Example 5 above and the acid acceptor 4-dimethylaminopyridine (DMAP) were dissolved in methylene chloride. The resulting solution was chilled to $-70°$ C. using a dry ice/acetone bath, and an equal molar amount of hexyl phosphorodichloridate (HOP) was slowly added. The reaction mixture was then heated and refluxed overnight. The salt formed in the polymerization was removed by filtration. The remaining polymer solution (filtrate) was washed with a saturated NaCl solution three times, and the homopolymer was precipitated in diethyl ether.

Example 10

Synthesis of Poly(phosphoester) P(BHDPT-HOP/TC)

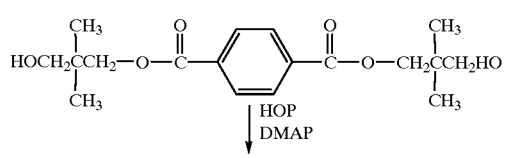

-continued

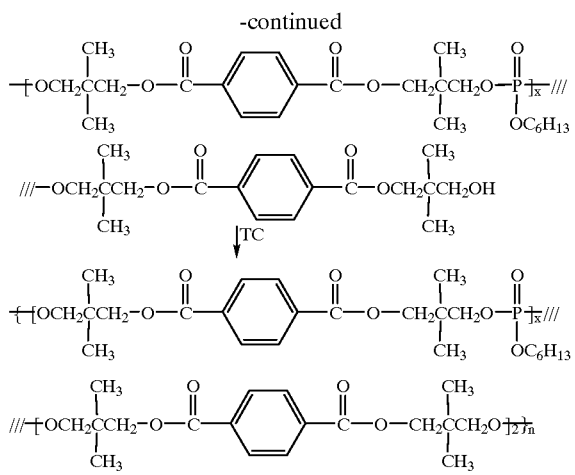

Copolymers of P(BHDPT-HOP) with TC were synthesized by a two-step solution polymerization. After the reaction between BHDPT and HOP had proceeded at room temperature for one hour, the reaction flask was cooled in a dry ice/acetone bath. An appropriate amount of TC (the number of moles of TC and HOP combined equaled the number of moles of BHDPT) was slowly added to the flask. The reaction mixture was then heated and refluxed overnight. The salt formed during the copolymerization was removed by filtration. The remaining copolymer solution (filtrate) was washed with a saturated NaCl solution three times, and the copolymer was precipitated out in diethyl ether.

Example 11

Other Diol Variations

Diol terephthalates that are structurally related to that of BHET and BHDPT were synthesized similarly to that in Example 5 by reacting TC with either n-propylenediol or 2-methylpropylenediol, the structures of which are shown below, to form the corresponding diol terephthalate.

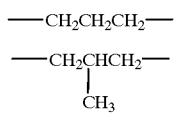

These diol terephthalates were then reacted with EOP to form the corresponding homopolymers. The homopolymers so formed were then used to produce the copolymers of the invention in a second reaction with TC, as described above in Example 7.

Example 12

Glass Transition Temperatures for P(BHET-EOP/TC) Copolymers

Figure 1B:
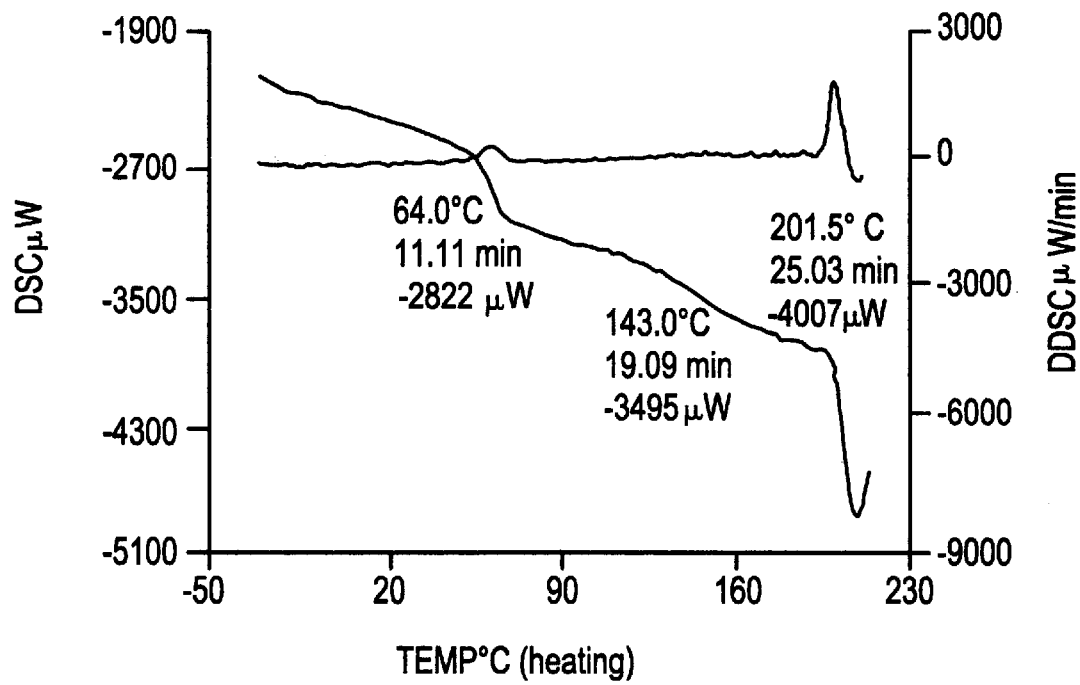
FIG. 1B shows the DSC curve of P(BHET-EOP/TC, 50/50).

By differential scanning calorimetry (DSC), the glass transition temperatures (Tg's) of P(BHET-EOP/TC, 80/20) and P(BHET-EOP/TC, 50/50) were determined to be 24.5° C. and 62.2° C. respectively. FIG. 1 shows the DSC curves for these two polymers. The Tg's of four additional P(BHET-EOP/TC) copolymers of differing EOP/TC feed ratios were determined, and the results were tabulated, as shown below in Table 3:

TABLE 3

Glass Transition Temperatures (Tg's) of (BHET-EOP/TC) Polymers

| Ratio of EOP/TC* | 100/0 | 95/5 | 90/10 | 85/15 | 80/20 | 50:50 |
|---|---|---|---|---|---|---|
| Tg (° C.) | 19.1 | 20.7 | 21.2 | 29.8 | 24.5 | 62.2 |

*Feed ratio of ethyl phosphorodichloridate to terephthaloyl chloride.

The Tg increased as the proportion of EOP decreased and the proportion of TC increased.

Example 14

Glass Transition Temperatures for P(BHDPT-EOP/TC) CoPolymers

A study of the influence of an increasing proportion of terephthaloyl chloride (TC) on the Tg's of P(BHDPT-EOP/TC) polymers was also conducted. The results are shown below in Table 4.

TABLE 4

Influence of EOP/TC Ratio on the Tg of P(BHDPT-EOP/TC)

| Molar ratio (BHDPT/EOP/TC)* | Tg (° C.) |
|---|---|
| 100:100:0 | 14 |
| 100:100:0 | 19 |
| 100:90:10 | 16 |
| 100:85:15 | 24 |
| 100:80:20 | 23 |
| 100:75:25 | 33 |
| 100:75:25 | 49 |
| 100:50:50 | 43 |

*The total molar amount of TC and EOP equaled the molar amount of BHDPT.

Example 15

Glass Transition Temperatures for Various R Groups

A study was also conducted showing the effect on glass transition temperature (Tg) for copolymers made from the following series of diols having varying R groups:

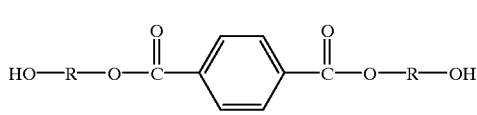

where R is —CH$_2$CH$_2$—; —CH$_2$CH$_2$CH$_2$—; —CH$_2$CH(CH$_3$)CH$_2$—; and —CH$_2$CH(CH$_3$)2CH$_2$—. The results are shown below in Table 5:

TABLE 5

Influence of the Changing "R" Group on Tg of Polymer

| "R" Group | Structure | Tg (° C.) |
|---|---|---|
| ethylene | —CH$_2$CH$_2$— | 14–19 |
| n-propylene | —CH$_2$CH$_2$CH$_2$— | −15 |

TABLE 5-continued

Influence of the Changing "R" Group on Tg of Polymer

| "R" Group | Structure | Tg (° C.) |
|---|---|---|
| 2-methylpropylene | —CH$_2$CHCH$_2$—<br>               \|<br>               CH$_3$ | 11 |
| 2,2'-dimethylpropylene |       CH$_3$<br>       \|<br>—CH$_2$CCH$_2$—<br>       \|<br>      CH$_3$ | 19 |

As shown in Table 5, the Tg increased as the size and the degree of branching of the R group increased. In addition, the polymers changed in physical state as the Tg changed. Specifically, as Tg increased, the polymers changed from rubbery to fine powders.

Example 16

Solubilities of the Polymers of the Invention

The solubility in organic solvents was determined for the homopolymer P(BHET-EOP, 100/0) and for the following block copolymers: P(BHET-EOP/TC, 95/5),

P(BHET-EOP/TC, 90/10),

P(BHET-EOP/TC, 85/15),

P(BHET-EOP/TC, 80/20), and

P(BHET-EOP/TC, 50/50).

The organic solvents used for the test were chloroform, methylene chloride, N-methylpyrrolidone (NMP), dimethylformamide (DMF) and dimethylsulfoxide (DMSO). The results of these solubility tests are summarized below in Table 6.

TABLE 6

| Polymer | CHCl$_3$ | CH$_2$Cl$_2$ | NMP | DMF | DMSO |
|---|---|---|---|---|---|
| P(BHET-EOP, 100/0) | Easily soluble | Easily soluble | Good solubility | Good solubility | Good solubility |
| P(BHET-EOP/TC, 95/5) | Easily soluble | Easily soluble | Good solubility | Good solubility | Good solubility |
| P(BHET-EOP/TC, 90/10) | Easily soluble | Easily soluble | Good solubility | Good solubility | Good solubility |
| P(BHET-EOP/TC, 85/15) | Relatively soluble | Relatively soluble | Good solubility | Good solubility | Good solubility |
| P(BHET-EOP/TC, 80/20) | Relatively soluble | Relatively soluble | Good solubility | Good solubility | Good solubility |
| P(BHET-EOP/TC, 50/50) | Not soluble | Not soluble | Soluble with heating | Soluble with heating | Soluble with heating |

The results showed that the solubility of these polymers in organic solvents increased as the EOP/TC ratio increased.

Example 16

Viscosities of the Polymers

The intrinsic viscosities of a series of P(BHET-EOP/TC) polymers of varying feed ratios were measured in chloroform (CH$_3$Cl) at 40° C. in a Ubbelohde viscometer. The results are shown below in Table 7.

TABLE 7

Intrinsic Viscosities of P(BHET-EOP/TC) Polymers

| Ratio of EOP/TC* | 100/0 | 95/5 | 90/10 | 85/15 | 80/20 | 50:50 |
|---|---|---|---|---|---|---|
| [η] (dL/g) | 0.081 | 0.089 | 0.148 | 0.146 | 0.180 | N.D.† |

*Feed ratio of ethyl phosphorodichloridate to terephthaloyl chloride.
†The intrinsic viscosity of P(BHET-EOP/TC, 50/50) was not determined because it was not soluble in chloroform.

Example 17

Physical Properties

Film sheets were prepared by solvent casting a series of P(BHET-EOP/TC) copolymers having various feed ratios. Both P(BHET-EOP/TC, 80/20) and P(BHET-EOP/TC, 85/15) copolymers exhibited good film forming properties. For these two copolymers, also, polymer fibers were successfully drawn from the copolymer melt at 160° C.

Example 18

Stability Testing (BHET-EOP/TC) copolymers of the invention were placed in a desiccator at room temperature, and their stability was monitored by intrinsic viscosity and GPC. The copolymers were stable under these conditions without the need for storage under inert gas.

Figure 6:
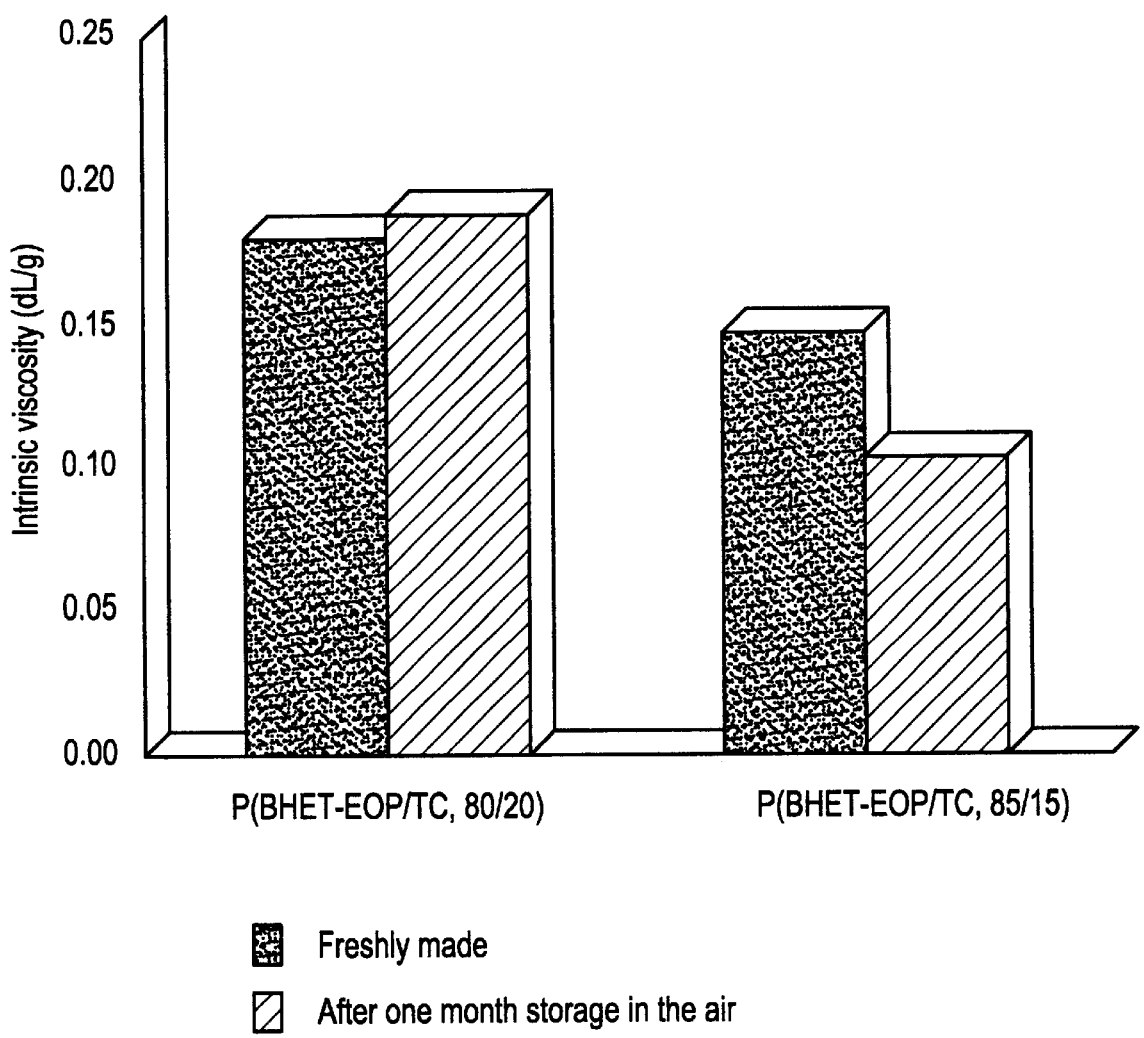
FIG. 6 shows the storage stability of P(BHET-EOP/TC, 80/20) and P(BHET-EOP/TC, 85/15).

Samples of P(BHET-EOP/TC 80/20) and P(BHET-EOP/TC 85/15) were also stored for one month in room air at room temperature. The stability was tested by intrinsic viscosity at the end of the one-month period, and the results are graphically represented in FIG. 6.

Example 19

In vitro Degradation

Films of P(BHET-EOP/TC, 80/20) and P(BHET-EOP/TC, 85/15) were made by solution casting methods, as prepared in Example 18, and were dried under vacuum for 2 days. Discs 1 mm in thickness and 6 mm in diameter were cut from these film sheets. Three discs of each copolymer were placed in 4 mL of phosphate buffer saline (PBS) (0.1M, pH 7.4) at 37° C. The discs were taken out of the PBS at different points in time, washed with distilled water, and dried overnight.

Figure 7A:
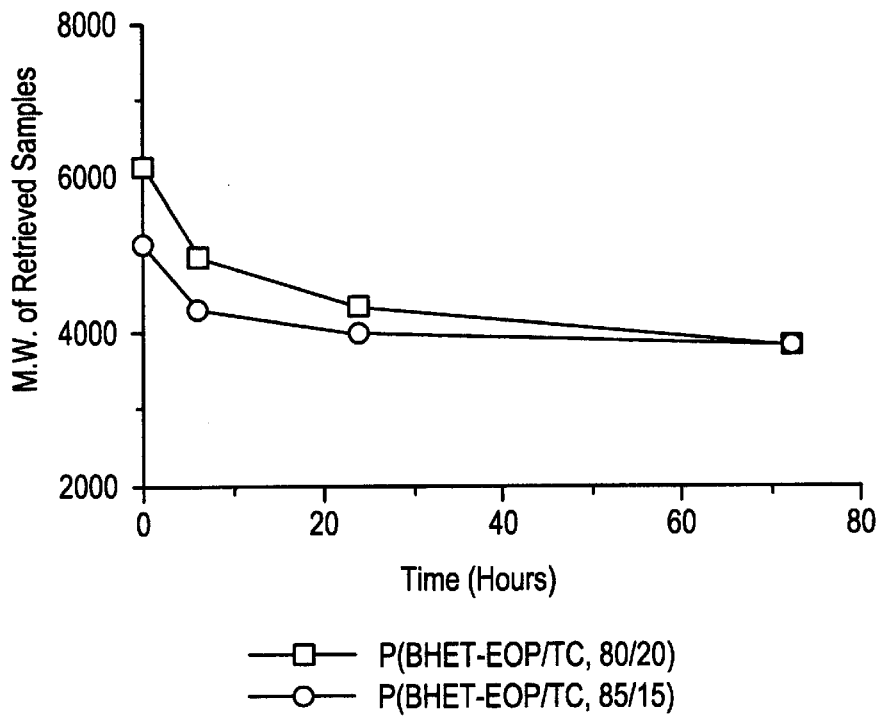
FIGS. 7A and 7B show the in vitro degradation data for P(BHET-EOP/TC, 80/20) and P(BHET-EOP/TC, 85/15).
Figure 7B:
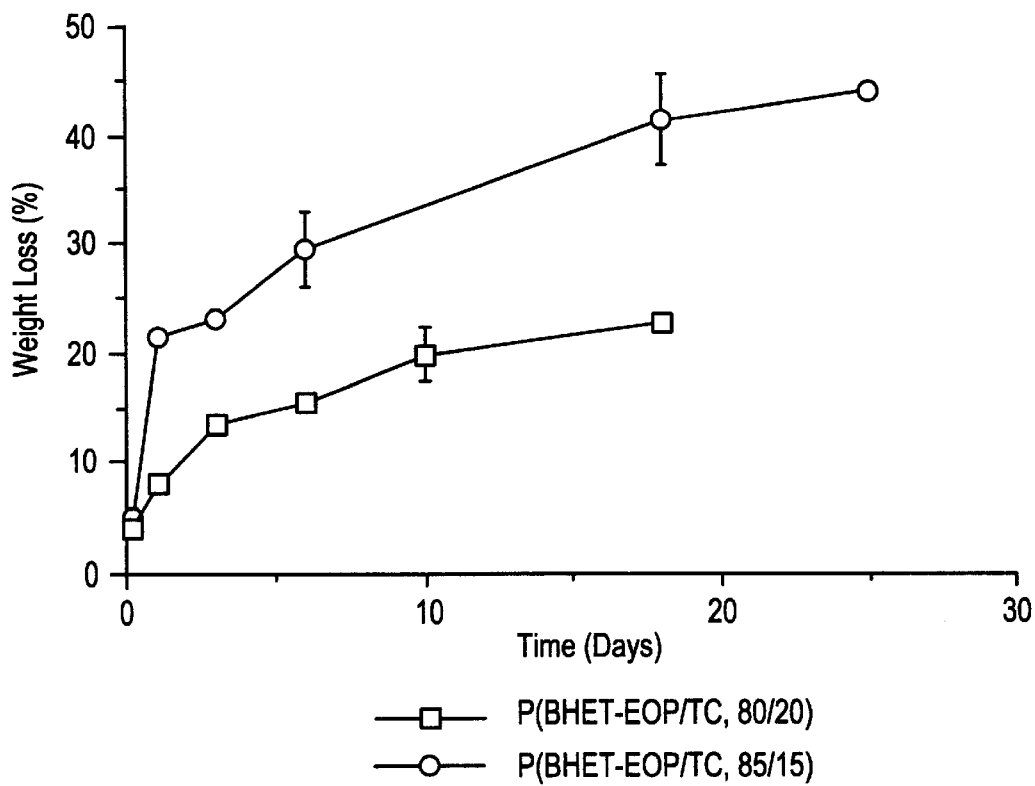

The samples were analyzed for change in molecular weight and weight loss over time, as shown in FIGS. 7A and 7B. The weight average molecular weight of P(BHET-EOP/TC, 80/20) decreased about 20% in three days. After 18 days, the P(BHET-EOP/TC, 85/15) and P(BHET-EOP/TC, 80/20) discs had lost about 40% and 20% in mass respectively.

This data demonstrated the feasibility of fine-tuning the degradation rate of the copolymers and confirmed that the copolymers became more hydrolytically labile as the phosphate component (EOP) was increased.

Figure 8:
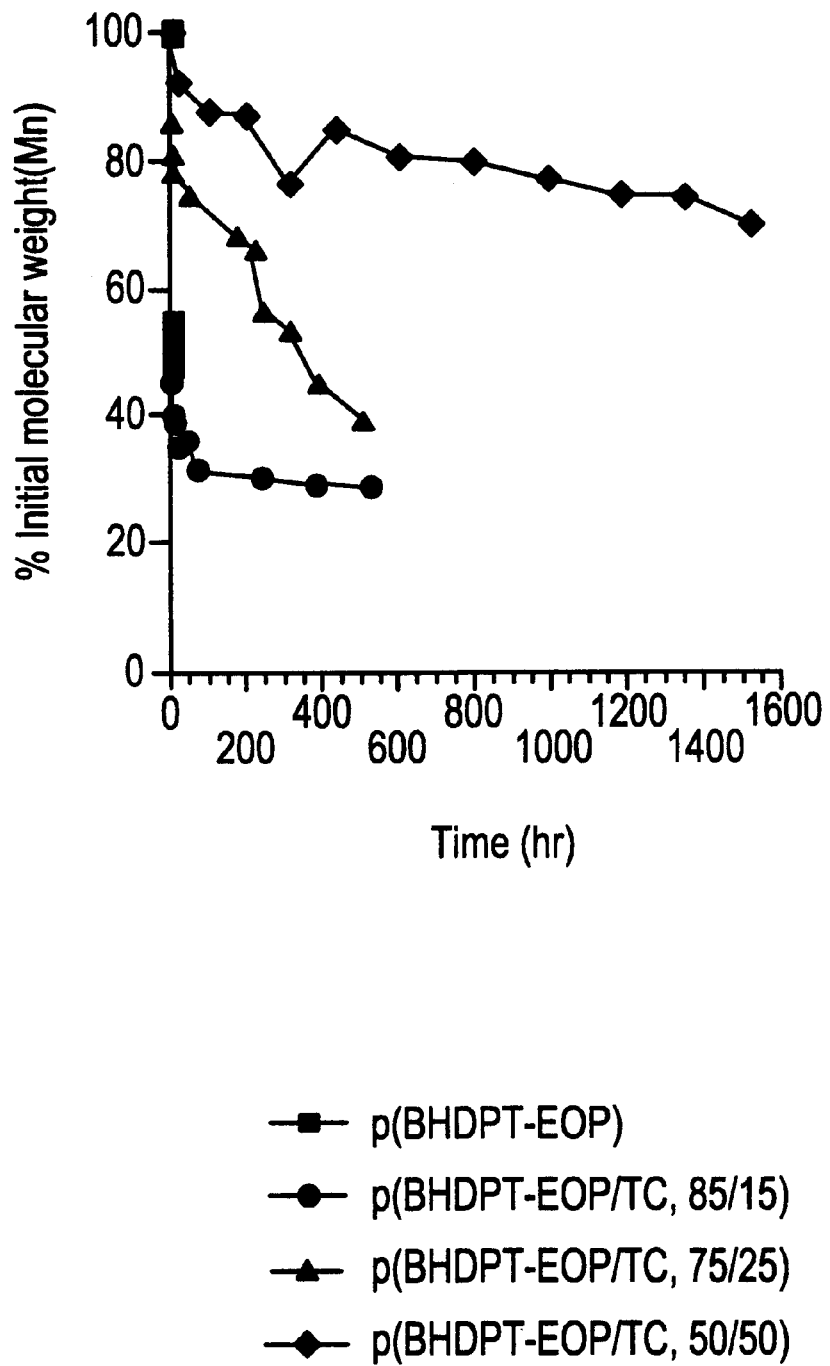
FIG. 8 shows the change in molecular weight of P(BHDPT-EOP) and P(BHDPT-EOP/TC) poly(phosphoesters) during in vitro degradation.

The same process was repeated for the P(BHDPT-EOP) polymers synthesized in Examples 6–8 above, including copolymers having different feed ratios of EOP to TC. FIG. 8 is a graphic representation of the degree of degradation, as measured by change in molecular weight, over time for the homopolymer P(BHDPT-EOP) and the following block copolymers:

P(BHDPT-EOP/TC, 85/15),
P(BHDPT-EOP/TC, 75/25), and
P(BHDPT-EOP/TC, 50/50).

Example 20

In vivo Degradation of P(BHET-EOP/TC) Copolymer

Figure 9:
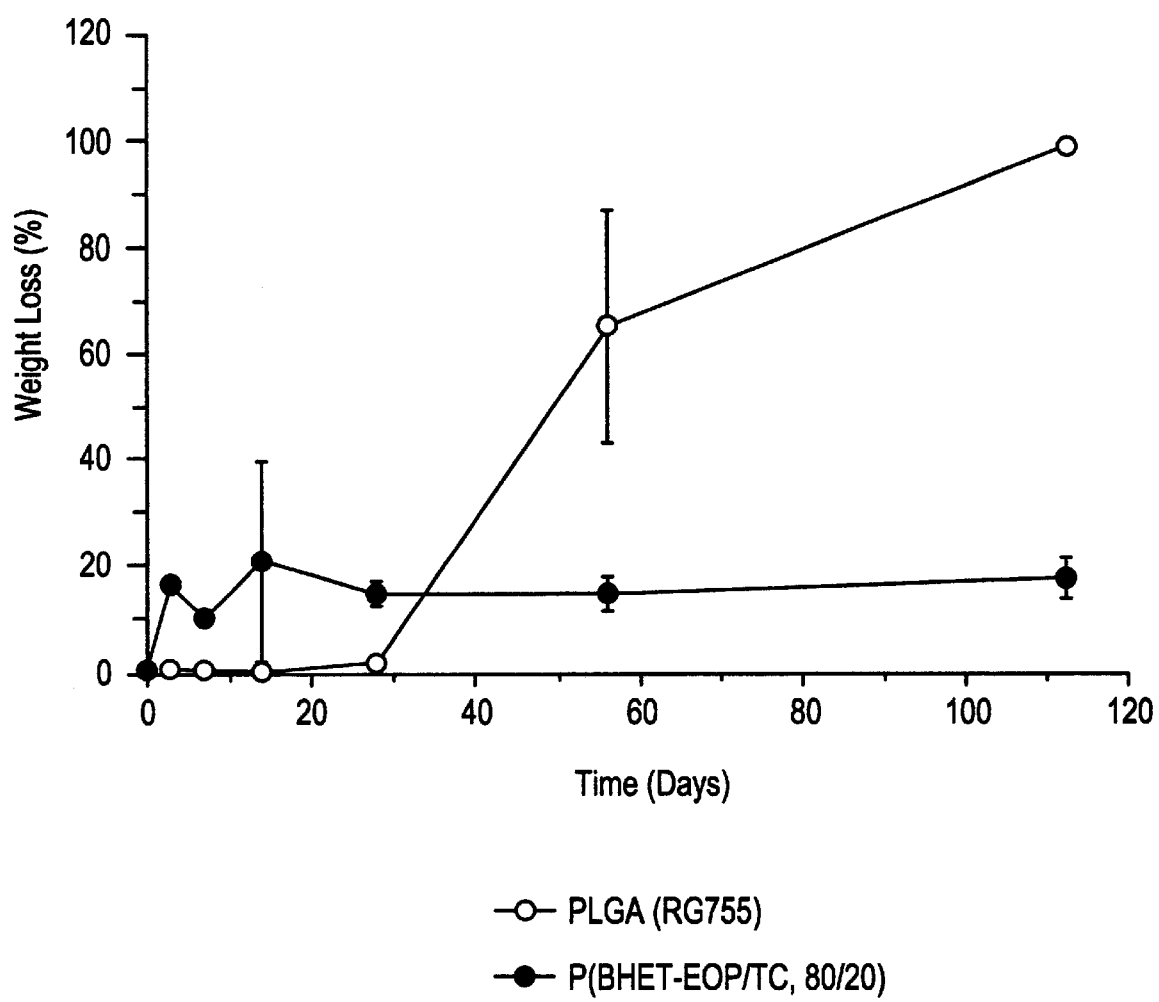
FIG. 9 shows the in vivo degradation of P(BHET-EOP/TC, 80/20) in terms of weight loss.

FIG. 9 shows the in vivo degradation of P(BHET-EOP/TC, 80/20), as measured by weight loss.

Example 21

In vitro Biocompatability/Cytotoxicity of P(BHET-EOP/TC, 80/20)

The cytotoxicity of P(BHET-EOP/TC, 80/20) copolymer was assessed by culturing human embryonic kidney (HEK) cells on a cover slip that had been coated with the copolymer P(BHET-EOP/TC, 80/20). As a control, HEK cells were also cultured on a coverslip coated with TCPS. The cells cultured on the copolymer-coated cover slip exhibited normal morphology at all times and proliferated significantly in 72 days, as compared to a considerably lower amount when identical HEK cells were cultured on TCPS.

Example 22

In vivo Biocompatibility of P(BHET-EOP/TC, 80/20)

A 100 mg polymer wafer was formed from P(BHET-EOP/TC, 80/20) and, as a reference, a copolymer of lactic and glycolic acid (75/25, "PLGA") known to be biocompatible. These wafers were inserted between muscle layers of the right limb of adult SPF Sprague-Dawley rats under anesthesia. The wafers were retrieved at specific times, and the surrounding tissues were prepared for histopathological analysis by a certified pathologist using the following scoring:

| Score | Level of Irritation |
| --- | --- |
| 0 | No Irritation |
| 0–200 | Slight Irritation |
| 200–400 | Mild Irritation |
| 400–600 | Moderate Irritation |
| More than 600 | Severe Irritation |

The results of the histopathological analysis are shown below in Table 8.

TABLE 8

| | Inflammatory Response at Site of Implantation (i.m.) | | | | | |
| --- | --- | --- | --- | --- | --- | --- |
| Polymer | 3 Days | 7 Days | 14 Days | 1 Month | 2 Mos. | 3 Mos. |
| P(BHET-EOP/TC, 80/20) | 151 | 116 | 163 | 98 | 60 | 35 |
| PLGA (75/25) | 148 | 98 | 137 | 105 | 94 | 43 |

The phosphoester copolymer P(BHET-EOP/TC, 80/20) was shown to have an acceptable biocompatibility similar to that exhibited by the PLGA reference wafer.

Example 23

Preparation of P(BHET-EOP/TC, 80/20) Microspheres Encapsulating FITC-BSA

Microspheres were prepared via a double-emulsion/solvent-extraction method using FITC-labeled bovine serum albumin (FITC-BSA) as a model protein drug. One hundred $\mu$L of an FITC-BSA solution (10 mg/mL) were added to a solution of 100 mg of P(BHET-EOP/TC, 80/20) in 1 mL of methylene chloride, and emulsified via sonication for 15 seconds on ice. The resulting emulsion was immediately poured into 5 mL of a vortexing aqueous solution of 1% polyvinyl alcohol (PVA) and 5% NaCl. The vortexing was maintained for one minute. The resulting emulsion was poured into 20 mL of an aqueous solution of 0.3% PVA and 5% NaCl, which was being stirred vigorously. Twenty-five mL of a 2% isopropanol solution was added, and the mixture was kept stirring for one hour to ensure complete extraction. The resulting microspheres were collected via centrifugation at 3000× g, washed three times with water, and lyophilized. Empty microspheres were prepared in the same way except that water was used as the inner aqueous phase.

Figure 10:
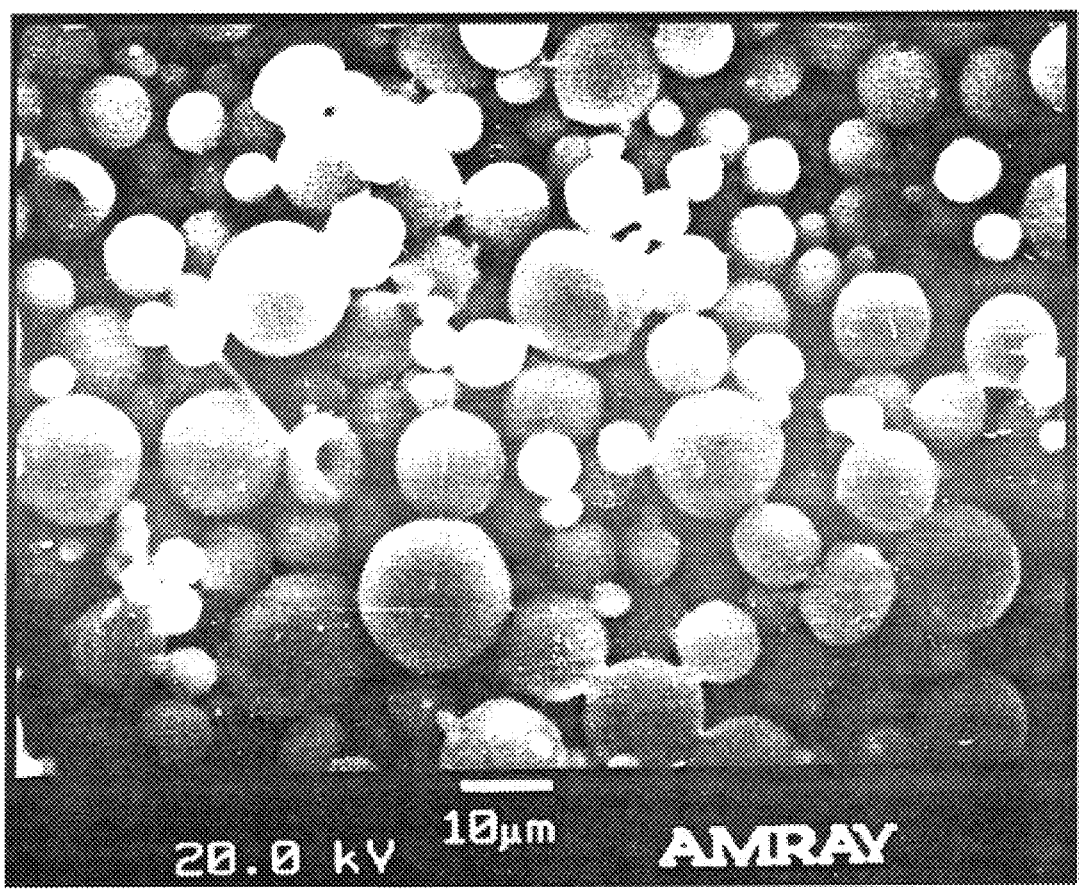
FIG. 10 shows an electron microscopic photograph of P(BHET-EOP/TC, 80/20) microspheres containing FITC-BSA.

These preparation conditions had been optimized for increased encapsulation efficiency, improved microsphere morphology, and minimal burst release. The resulting microspheres were mostly between 5 and 20 $\mu$m in diameter and exhibited a smooth surface morphology. FIG. 10 shows the size and smoothness of the microspheres, as demonstrated by electron microscopy.

The loading level of FITC-BSA was determined by assaying for FITC after hydrolyzing the microspheres in a 0.5 N NaOH solution overnight. Loading levels were determined by comparison with a standard curve, which had been generated by making a series of FITC-BSA solutions in 0.5 N NaOH. Protein loading levels of 1.5, 14.1 and 22.8 wt. % were readily obtained.

The encapsulation efficiency of FITC-BSA by the microspheres was determined at different loading levels by comparing the quantity of FITC-BSA entrapped with the initial amount in solution via fluorometry. As shown below in Table 9, encapsulation efficiencies of 84.6 and 99.6% were obtained. These results showed that encapsulation efficiencies of 70–90% would be readily obtainable.

TABLE 9

Encapsulation Efficiency and Loading Level of FITC-BSA in P(BHET-EOP/TC, 80/20)

| Loading (%) | High Loading (22.8%) | Low Loading (1.5%) |
| --- | --- | --- |
| Encapsulation Efficiency (%) | 99.6 | 84.6 |

In addition, it was determined by observation with confocal fluorescence microscopy that the encapsulated FITC-BSA was distributed uniformly within the microspheres.

Example 24

Preparation of P(BHDPT-EOP/TC, 50/50) Microspheres Containing Lidocaine

An aqueous solution of 0.5% w/v polyvinyl alcohol (PVA) was prepared in a 600 mL beaker by combining 1.35 g of PVA with 270 mL of deionized water. The solution was stirred for one hour and filtered. A copolymer/drug solution was prepared by combining 900 mg of P(BHDPT-EOP/TC, 50/50) copolymer and 100 mg of lidocaine in 9 mL of methylene chloride and vortex-mixing.

While the PVA solution was being stirred at 800 rpm with an overhead mixer, the polymer/drug mixture was added dropwise. The combination was stirred for one and a half hours. The microspheres thus formed were then filtered, washed with deionized water, and lyophilized overnight. The experiment yielded 625 mg of microspheres loaded with 3.7% w/w lidocaine.

Lidocaine-containing microspheres were also prepared from P(BHDPT-HOP/TC, 50/50) by the same process. This experiment yielded 676 mg of microspheres loaded with 5.3% w/w lidocaine.

Example 25

In vitro Release Kinetics of Microspheres Prepared from P(BHET-EOP/TC, 80/20) Copolymers Five mg of P(BHET-EOP/TC, 80/20) microspheres containing FITC-BSA were suspended in one mL of phosphate buffer saline (PBS) at pH 7.4 and placed into a shaker heated to a temperature of 37° C. At various points in time, the suspension was spun at 3000× g for 10 minutes, and 500 μl samples of the supernatant fluid were withdrawn and replaced with fresh PBS. The release of FITC-BSA from the microspheres was followed by measuring the fluorescence intensity of the withdrawn samples at 519 nm.

Scaling up, 50 mg of P(BHET-EOP/TC, 80/20) microspheres were suspended in vials containing 10 mL of phosphate buffer saline (PBS). The vials were heated in an incubator to a temperature of 37° C. and shaken at 220 rpm. Samples of the supernatant were withdrawn and replaced at various points in time, and the amount of FITC-BSA released into the samples was analyzed by spectrophotometry at 492 nm.

Figure 11:
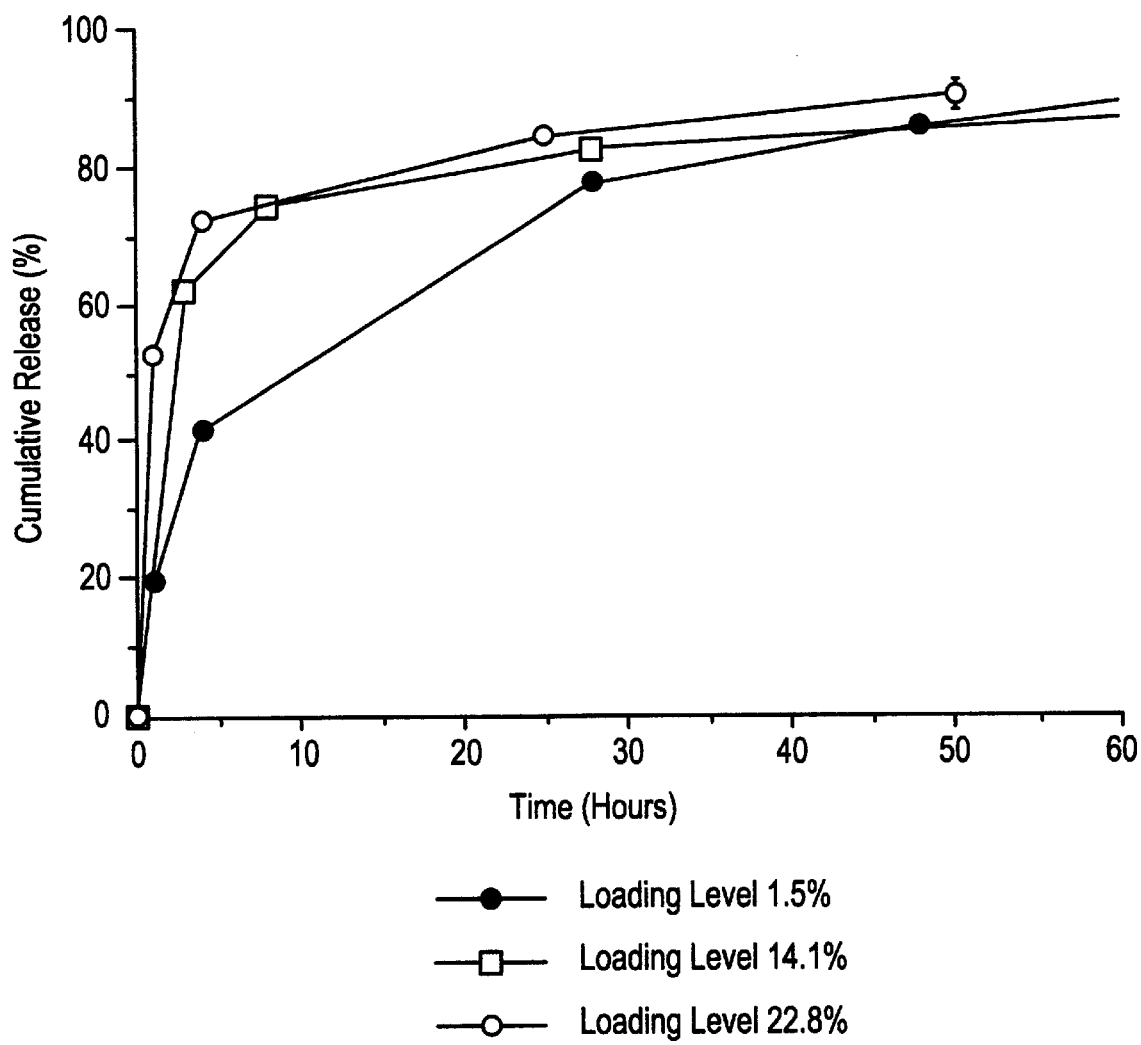
FIG. 11 shows the effect of loading level on the release kinetics of FITC-BSA from microspheres.

The results indicated that over 80% of the encapsulated FITC-BSA was released within the first two days, with an additional amount of about 5% being released after 10 days in PBS at 37° C. The release kinetics of FITC-BSA from P(BHET-EOP/TC, 80/20) microspheres at different loading levels are shown in FIG. 11.

Example 26

Figure 12:
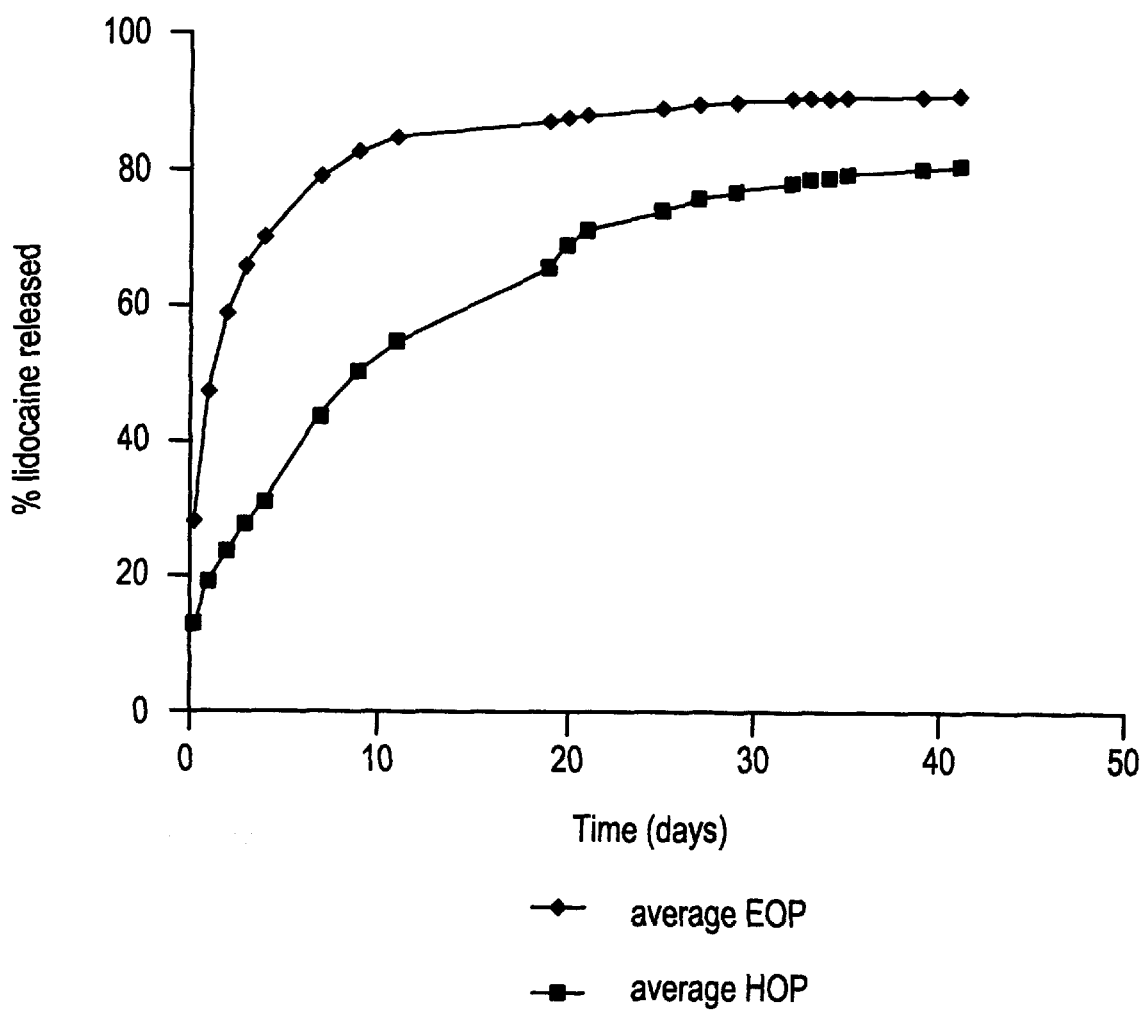
FIG. 12 shows the lidocaine release from polymer BHDPT-EOP and BHDPT-HOP microspheres.
Figure 13:
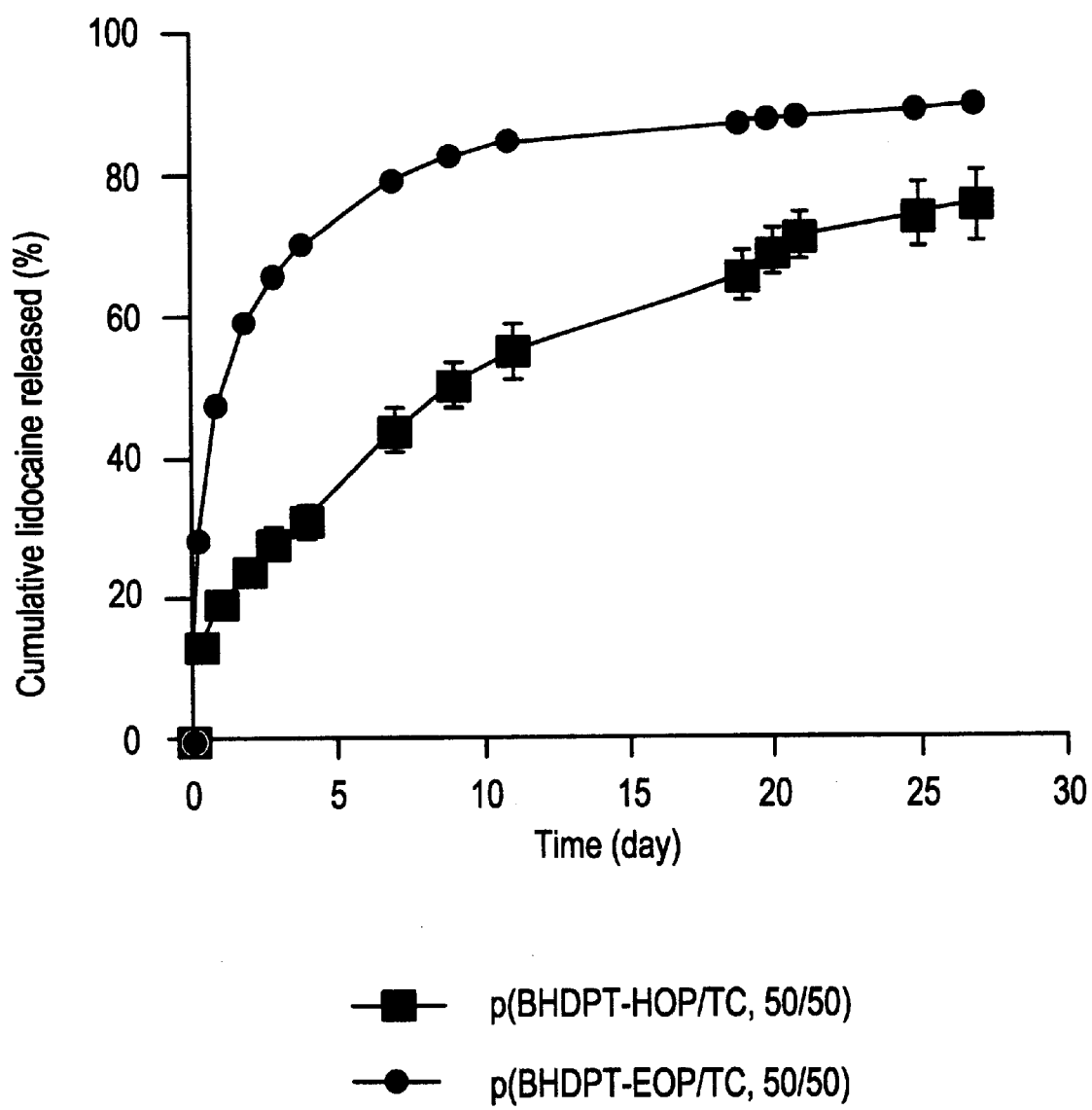
FIG. 13 shows the release of lidocaine from copolymer P(BHDPT-EOP/TC) microspheres.

In vitro Release Kinetics of Microspheres Prepared from P(BHDPT-EOP/TC, 50/50) Copolymers Approximately 10 mg of P(BHDPT-EOP/TC, 50/50) microspheres loaded with lidocaine were placed in PBS (0.1 M, pH 7.4) at 37° C. on a shaker. Samples of the incubation solution were withdrawn periodically, and the amount of lidocaine released into the samples was assayed by HPLC. FIGS. 12 and 13 show the resulting release kinetics.

The same process was followed for microspheres prepared from P(BHDPT-HOP/TC, 50/50). FIGS. 12 and 13 also show the release kinetics of lidocaine from these microspheres.

Example 27

In vitro Cytotoxicity Assay of Copolymer on Cells

Figure 14:
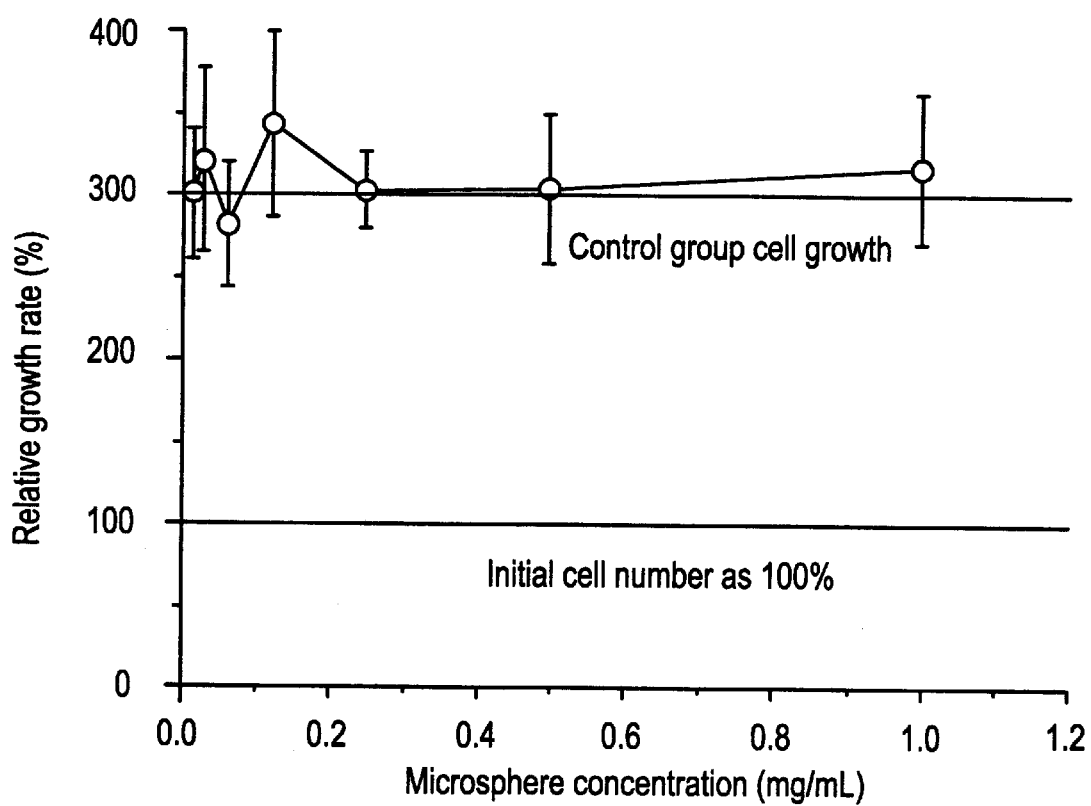
FIG. 14 shows the cytotoxicity of P(BHET-EOP/TC, 80/20) microspheres.

P(BHET-EOP/TC, 80/20) microspheres were added to 96-well tissue culture plates at different concentrations. The wells were then seeded with human gastric carcinoma cells (GT3TKB) at a density of $10^4$ cells/well. The cells were incubated with the microspheres for 48 hours at 37° C. The resulting cell proliferation rate was analyzed by MTT assay and plotted as % relative growth vs. concentration of copolymer microspheres in the tissue culture well. The results are shown in FIG. 14.

Example 28

Toxicity Assay of Polymer-Degradation Products on GT3TKB Tumor Cells

About 100–150 mg of each of the following polymers were degraded separately in 20 mL of 1M NaOH at 370C for 1–2 days:

PLLA (Mw=14,000)
P(BHET-EOP)
PCPP:SA (20:80)
Poly(L-lysine) (Mw=88,000)

Complete degradation was observed for all of the polymers. The solution was then neutralized with 20 mL of 1M HCl.

Figure 15:
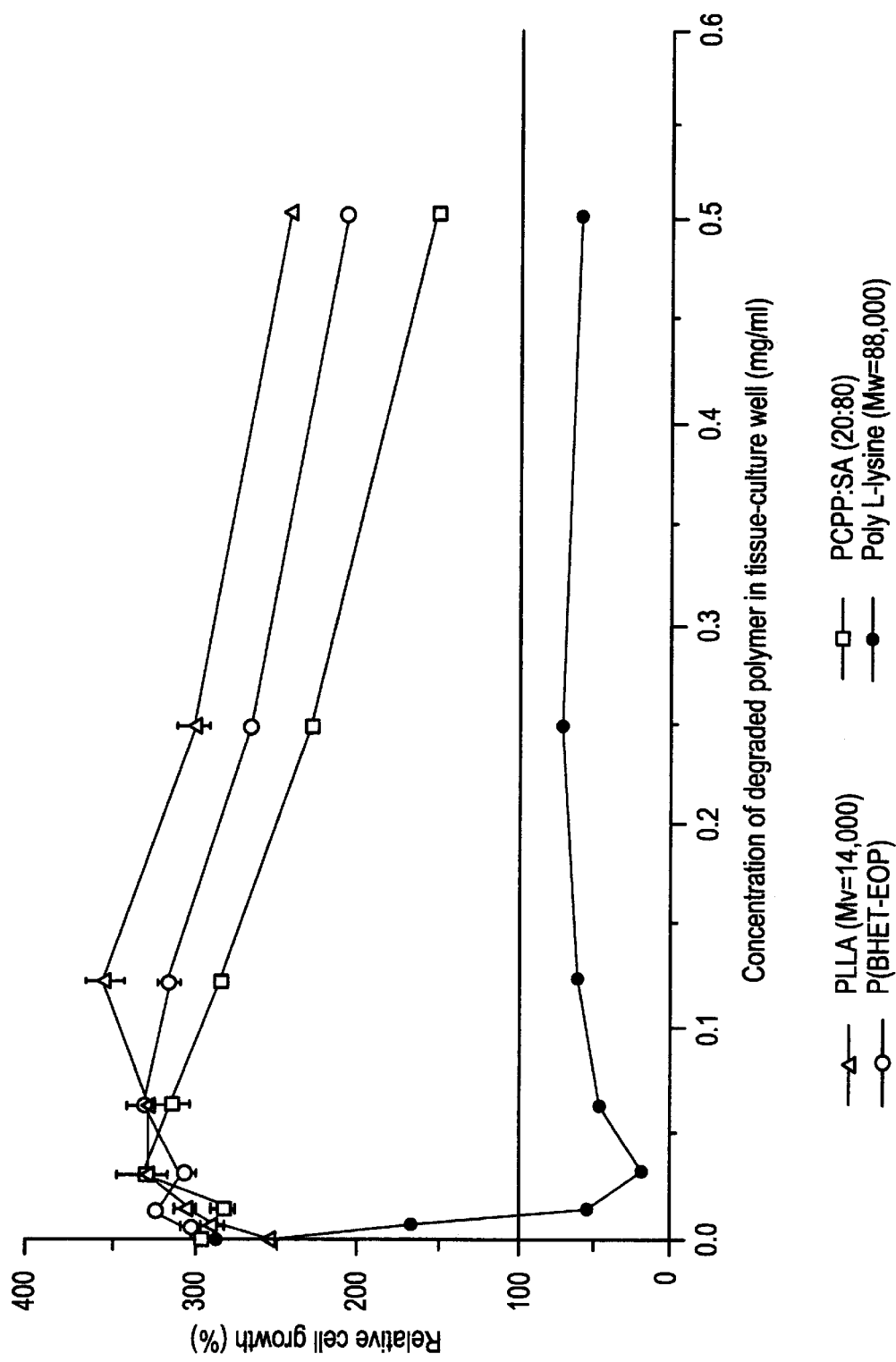
FIG. 15 shows a toxicity assay plot of relative cell growth (%) vs. concentration of degraded polymer in a tissue-culture well (mg/ml) for four separate polymers.

About 200 μL of various concentrations of the degraded polymer products were placed in 96-well tissue culture plates and seeded with human gastric carcinoma cells (GT3TKB) at a density of $10^4$/well. The degraded polymer products were incubated with the GT3TKB cells for 48 hours. The results of the assay were plotted as % relative growth vs. concentration of degraded polymer in the tissue-culture well and are shown in FIG. 15.

Figure 16:
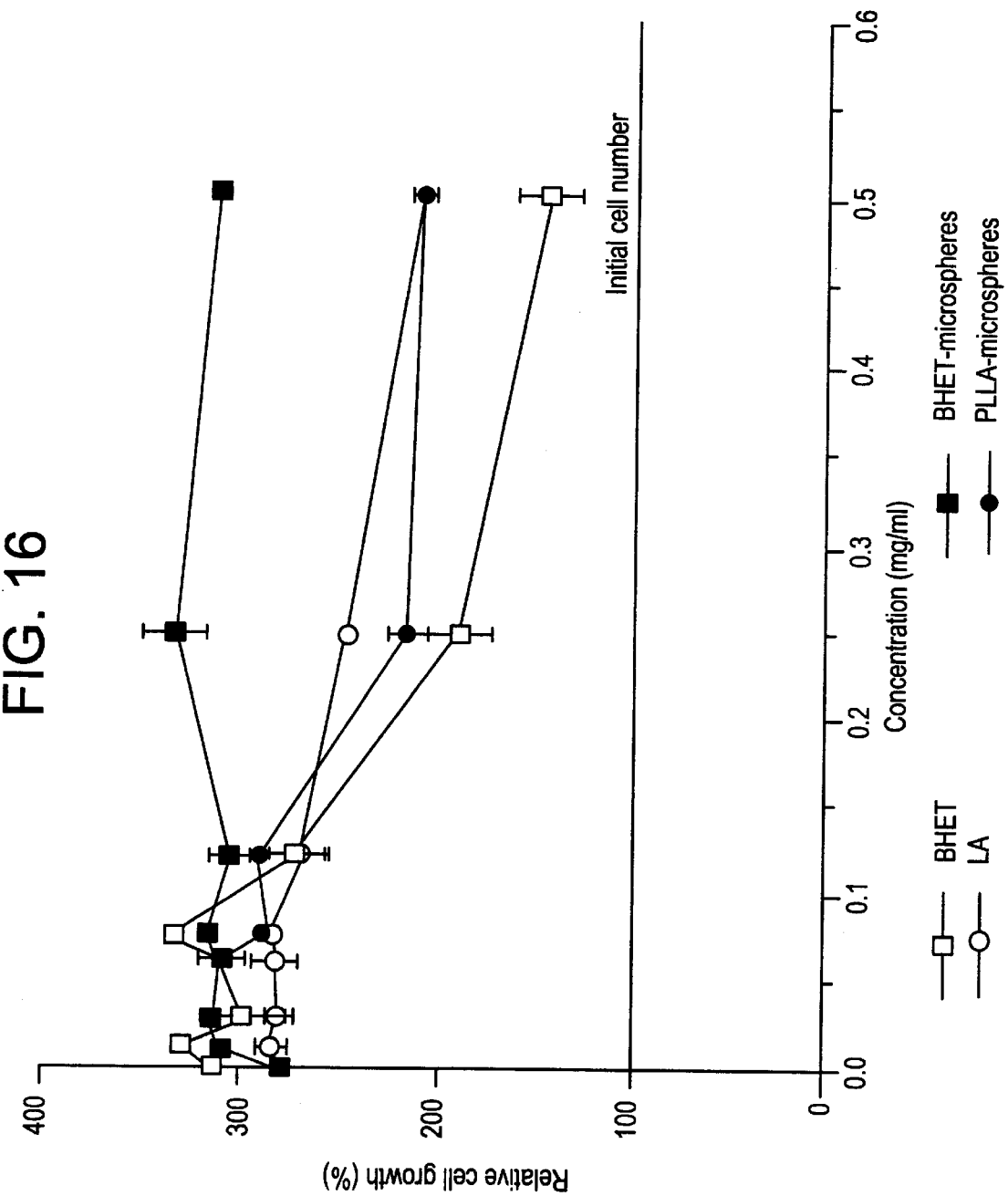
FIG. 16 shows a cell toxicity assay plot for two microspheres and their respective monomers.

An additional toxicity assay was conducted with microspheres prepared from the monomer BHET and from the homopolymer BHET-EOP, and compared with microspheres prepared from LA and PLLA. The results of the assay were plotted as % relative growth vs. concentration of the polymers or microspheres in a tissue-culture cell and are shown in FIG. 16.

The invention being thus described, it will be obvious that the same may be varied in many ways. Such variations are not to be regarded as a departure from the spirit and scope of the invention, and all such modifications are intended to be included within the scope of the following claims.

We claim:

1. A biodegradable terephthalate polymer comprising the recurring monomeric units shown in formula I:

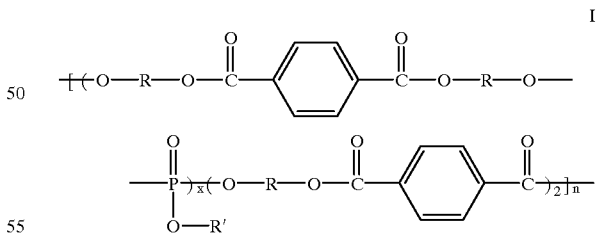

wherein R is a divalent organic moiety;

R' is an aliphatic, aromatic or heterocyclic residue;

x is a 1; and n=1–5,000, wherein said biodegradable polymer is biocompatible before and upon biodegradation.

2. The polymer of claim 1 wherein R is an alkylene group, a cycloaliphatic group, a phenylene group, or a divalent group having the formula:

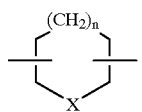

wherein X is oxygen, nitrogen, or sulfur, and
n is 1 to 3.

3. The polymer of claim 1 wherein R is an alkylene group having from 1 to 7 carbons atoms.

4. The polymer of claim 1 wherein R is an ethylene group.

5. The polymer of claim 1 wherein R is an n-propylene group.

6. The polymer of claim 1 wherein R is 2-methylpropylene.

7. The polymer of claim 1 wherein R is 2,2'-dimethylpropylene.

8. The polymer of claim 1 wherein R' is an alkyl group or a phenyl group.

9. The polymer of claim 1 wherein R' is an alkyl group having from 1 to 7 carbon atoms.

10. The polymer of claim 1 wherein R' is an ethyl group.

11. The polymer of claim 1 wherein x is from about 1 to about 30.

12. The polymer of claim 1 wherein x is from about 1 to about 20.

13. The polymer of claim 1 wherein x is from about 2 to about 20.

14. The polymer of claim 1 wherein said polymer is prepared by solution polymerization.

15. The polymer of claim 1 wherein said polymer comprises additional biocompatible monomeric units.

16. The polymer of claim 1 wherein said polymer is soluble in at least one of the solvents selected from the group consisting of acetone, dimethylene chloride, chloroform, ethyl acetate, DMAC, N-methyl pyrrolidone, dimethylformamide and dimethylsulfoxide.

17. A process for preparing a biodegradable terephthalate homopolymer comprising the recurring monomeric units of formula I:

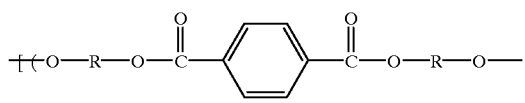

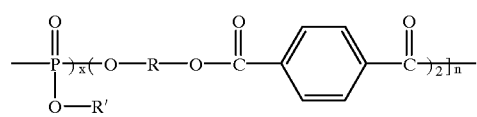

wherein R is a divalent organic moiety;

R' is an aliphatic, aromatic or heterocyclic residue;

x is $\geq 1$; and n=1–5,000, wherein said biodegradable polymer is biocompatible before and upon biodegradation, said process comprising the step of polymerizing p moles of a diol compound having formula II:

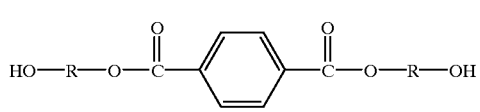

wherein R is as defined above, with q moles of a phosphorodichloridate of formula III:

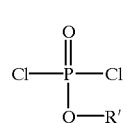

wherein R' is defined as above, and p>q, to form q moles of a homopolymer of formula IV, shown below:

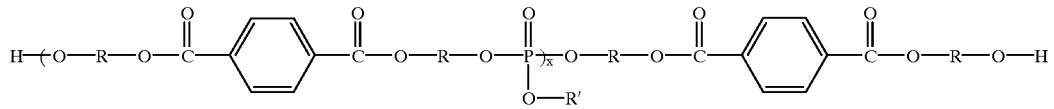

wherein R, R' and x are as defined above.

18. The process of claim 17 wherein R is an alkylene group having from 1 to 7 carbon atoms.

19. The process of claim 17 wherein R is an ethylene group.

20. The process of claim 17 wherein R is an n-propylene group.

21. The process of claim 17 wherein R is 2-methylpropylene.

22. The process of claim 17 wherein R is 2,2'-dimethylpropylene.

23. The process of claim 17 wherein R' is an alkyl group having from 1 to 7 carbon atoms.

24. The process of claim 17 wherein R' is an ethyl group.

25. The process of claim 17 wherein x is from about 1 to about 40.

26. The process of claim 17 wherein said polymerization reaction takes place at a temperature about −40 to about +160° C.

27. The process of claim 17 wherein the temperature of the polymerization varies from about 0 to 65° C.

28. The process of claim 17 wherein said polymerization takes place during a time between about 30 minutes and 24 hours.

29. The process of claim 17 wherein said polymerization is a solution polymerization reaction.

30. The process of claim 17 wherein an acid acceptor is present.

31. The process of claim 17 wherein the acid acceptor is a tertiary amine.

32. A process for preparing a biodegradable terephthalate polymer comprising the recurring monomeric units of formula I:

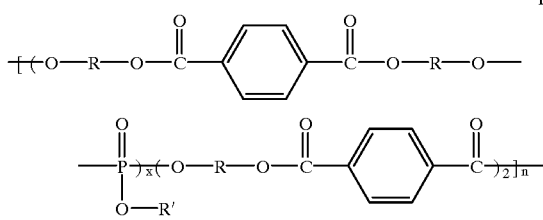

wherein R is a divalent organic moiety;
R' is an aliphatic, aromatic or heterocyclic residue;
x is $\geq 1$; and
n=1–5,000,
wherein said biodegradable polymer is biocompatible before and upon biodegradation, said process comprising the steps of:
(a) polymerizing p moles of a diol compound having formula II:

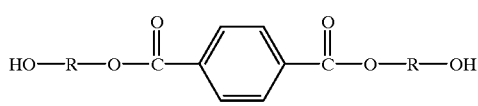

wherein R is as defined above, with q moles of a phosphorodichloridate of formula III:

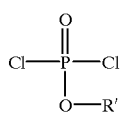

wherein R' is defined as above, and p>q, to form q moles of a polymer of formula IV, shown below:

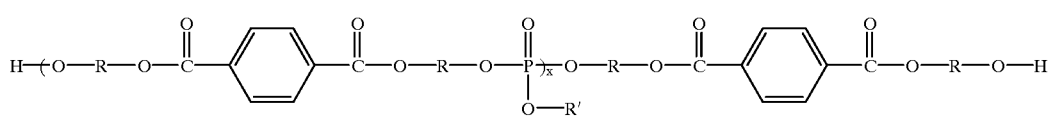

wherein R, R' and x are as defined above; and
(b) further reacting said polymer of formula IV and excess diol of formula II with (p−q) moles of terephthaloyl chloride having the formula V:

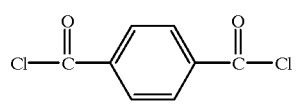

to form said polymer of formula I.

33. The process of claim 32 wherein R is an alkylene group having from 1 to 7 carbon atoms.
34. The process of claim 32 wherein R is an ethylene group.
35. The process of claim 32 wherein R is an n-propylene group.
36. The process of claim 32 wherein R is 2-methylpropylene.
37. The process of claim 32 wherein R is 2,2'-dimethylpropylene.
38. The process of claim 32 wherein R' is an alkyl group having from 1 to 7 carbon atoms.
39. The process of claim 32 wherein R' is an ethyl group.
40. The process of claim 32 wherein x is from about 1 to 30.
41. The process of claim 32 wherein x is from about 2 to about 20.
42. The process of claim 32 wherein said polymerization reaction of step (a) takes place at a temperature about −40 to about +160° C.
43. The process of claim 32 wherein the temperature of the polymerization step (a) varies from about 0 to 65° C.
44. The process of claim 32 wherein said polymerization step (a) takes place during a time between about 30 minutes and 24 hours.
45. The process of claim 32 wherein said polymerization step (a) is a solution polymerization reaction.
46. The process of claim 32 wherein an acid acceptor is present during said polymerization step (a).
47. The process of claim 32 wherein the acid acceptor is a tertiary amine.
48. The process of claim 32 wherein said copolymerization of step (b) takes place at a temperature between about −40 and 100° C.
49. The process of claim 32 wherein said copolymerization of step (b) takes place during a time of about 30 minutes to 24 hours.
50. The process of claim 32 wherein said polymer of formula I is purified by quenching a solution of said polymer with a non-solvent or a partial solvent.
51. A biosorbable suture comprising the polymer of claim 1.
52. An orthopedic appliance, bone cement or bone wax for repairing injuries to bone and connective tissue comprising the polymer of claim 1.
53. A laminate for degradable or non-degradable fabrics comprising the polymer of claim 1.
54. A coating for an implantable device comprising the polymer of claim 1.
55. A biodegradable terephthalate polymer composition comprising:
(a) at least one biologically active substance and
(b) a polymer having the recurring monomeric units shown in formula I:

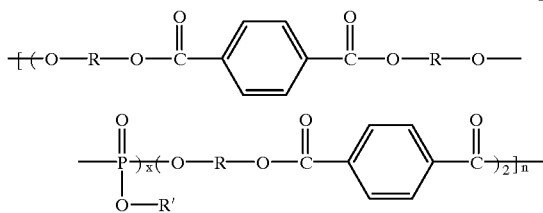

wherein R is a divalent organic moiety;
R' is an aliphatic, aromatic or heterocyclic residue;
x is ≧1;
n=1–5,000; and
said polymer is biocompatible before and upon biodegradation.

56. The polymer composition of claim 55 wherein R is an alkylene group, a cycloaliphatic group, a phenylene group, or a divalent group having the formula:

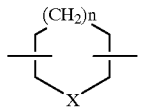

wherein X is oxygen, nitrogen, or sulfur,
and n is 1 to 3.

57. The polymer composition of claim 55 wherein R is an ethylene group.

58. The polymer composition of claim 55 wherein R is an n-propylene group.

59. The polymer composition of claim 55 wherein R is 2-methylpropylene.

60. The polymer composition of claim 55 wherein R is 2,2'-dimethylpropylene.

61. The polymer composition of claim 55 wherein R' is an alkyl group or a phenyl group.

62. The polymer composition of claim 55 wherein R' is an ethyl group.

63. The polymer composition of claim 55 wherein x is from about 1 to about 30.

64. The polymer composition of claim 55 wherein said copolymer is prepared by solution polymerization.

65. The polymer composition of claim 55 wherein said polymer comprises additional biocompatible monomeric units.

66. The polymer composition of claim 55 wherein said polymer is soluble in at least one of the solvents selected from the group consisting of acetone, dimethylene chloride, chloroform, ethyl acetate, DMAC, N-methyl pyrrolidone, dimethylformamide and dimethylsulfoxide.

67. The polymer composition of claim 55 wherein said biologically active substance is selected from the group consisting of peptides, polypeptides, proteins, amino acids, polysaccharides, growth factors, hormones anti-angiogenesis factors, interferons or cytokines, and pro-drugs of these substances.

68. The polymer composition of claim 55 wherein said biologically active substance is a therapeutic drug or pro-drug.

69. The polymer composition of claim 68 wherein said drug is selected from the group consisting of anti-neoplastic agents, antibiotics, anti-virals, antifungals, anti-inflammatories, and anticoagulants.

70. The polymer composition of claim 55 wherein said biologically active substance and said polymer form a homogeneous matrix.

71. The polymer composition of claim 55 wherein said polymer is characterized by a release rate of the biologically active substance in vivo controlled at least partially as a function of hydrolysis of the phosphoester bond of the polymer during biodegradation.

72. An article useful for implantation, injection, or otherwise placed totally or partially within the body, said article comprising a biodegradable terephthalate polymer composition comprising:
(a) at least one biologically active substance and
(b) a polymer having the recurring monomeric units shown in formula I:

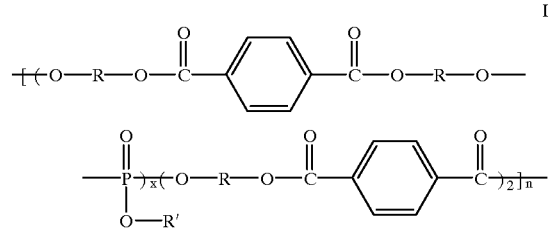

wherein R is a divalent organic moiety;
R' is an aliphatic, aromatic or heterocyclic residue;
x is ≧1; and
n=1–5,000,
wherein said polymer is sufficiently pure to make the biodegradable composition biocompatible upon biodegradation.

73. The article of claim 72 wherein R is an alkylene group, a cycloalkylene group, a phenylene group, or a divalent group having the formula:

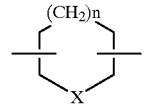

wherein X is oxygen, nitrogen, or sulfur, and n is 1 to 3.

74. The article of claim 72 wherein R is an ethylene group.

75. The article of claim 72 wherein R is an n-propylene group.

76. The article of claim 72 wherein R is 2-methylpropylene.

77. The article of claim 72 wherein R is 2,2'-dimethylpropylene.

78. The article of claim 72 wherein R' is an alkyl group or a phenyl group.

79. The article of claim 72 wherein R' is an ethyl group.

80. The article of claim 72 wherein x is from about 1 to about 30.

81. The article of claim 72 wherein x is from about 2 to 20.

82. The article of claim 72 wherein said polymer is prepared by solution polymerization.

83. The article of claim 72 wherein said polymer comprises additional biocompatible monomeric units.

84. The article of claim 72 wherein said polymer is soluble in at least one of the solvents selected from the group consisting of acetone, dimethylene chloride, chloroform, ethyl acetate, DMAC, N-methyl pyrrolidone, dimethylformamide and dimethylsulfoxide.

85. The article of claim 72 wherein said biologically active substance is selected from the group consisting of peptides, polypeptides, proteins, amino acids, polysaccharides, growth factors, hormones, anti-angiogenesis factors, interferons or cytokines, and pro-drugs of these substances.

86. The article of claim 72 wherein said biologically active substance is a therapeutic drug or pro-drug.

87. The article of claim 86 wherein said biologically active substance is selected from the group consisting of anti-neoplastic agents, antibiotics, anti-virals, antifungals, anti-inflammatories, anticoagulants, and pro-drugs of these substances.

88. The article of claim 72 wherein said biologically active substance and said polymer form a homogeneous matrix.

89. The article of claim 72 wherein said biologically active substance is encapsulated within said polymer.

90. The article of claim 72 wherein said polymer is characterized by a release rate of the biologically active substance in vivo controlled at least partially as a function of hydrolysis of the phosphoester bond of the polymer upon biodegradation.

91. The article of claim 72 wherein said article is adapted for implantation or injection into the body of an animal.

92. The article of claim 72 wherein said article results in minimal tissue irritation when implanted or injected into vasculated tissue.

93. The article of claim 72 wherein said article is in the form of a laminate for degradable fabric.

94. The article of claim 72 wherein said article is in the form of a biosorbable suture, a material for repairing bone injuries, or a coating on an implant device.

95. A method for the controlled release of a biologically active substance comprising the steps of:
(a) combining the biologically active substance with a biodegradable terephthalate polymer having the recurring monomeric units shown in formula I:

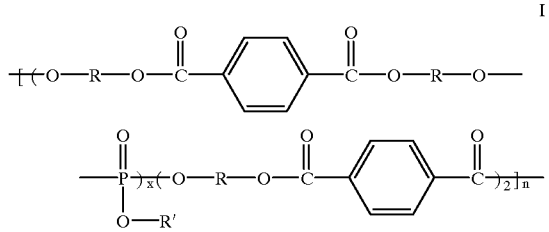

wherein R is a divalent organic moiety;
R' is an aliphatic, aromatic or heterocyclic residue;
x is ≧1; and
n=1–5,000,
wherein said polymer is biocompatible before and upon biodegradation, to form an admixture;
(b) forming said admixture into a shaped, solid article; and
(c) implanting or injecting said solid article in vivo at a preselected site, such that the solid implanted or injected matrix is in at least partial contact with a biological fluid.

96. The method of claim 95 wherein R is an ethylene group.

97. The method of claim 96 wherein R is an n-propylene group.

98. The method of claim 96 wherein R is 2-methylpropylene.

99. The method of claim 96 wherein R is 2,2'-dimethylpropylene.

100. The method of claim 96 wherein R' is an ethyl group.

101. The method of claim 96 wherein x is from about 1 to about 30.

102. The method of claim 96 wherein the ratio is from about 10:1 to about 1:1.

103. The method of claim 96 wherein said polymer comprises additional biocompatible monomeric units.

104. The method of claim 96 wherein said biologically active substance is selected from the group consisting of peptides, polypeptides, proteins, amino acids, polysaccharides, growth factors, hormones, anti-angiogenesis factors and other anti-neoplastic agents, interferons or cytokines, and pro-drugs of these substances.

105. The method of claim 96 wherein said biologically active substance is a therapeutic drug or pro-drug.

106. The method of claim 96 wherein said drug is selected from the group consisting of chemotherapeutic agents, antibiotics, anti-virals, antifungals, anti-inflammatories, and anticoagulants.

107. The method of claim 96 wherein said biologically active substance and said polymer form a homogeneous matrix.

108. The method of claim 96 further comprising encapsulating said biologically active substance within said polymer.

109. The method of claim 96 wherein said polymer is characterized by a release rate of the biologically active substance in vivo controlled at least partly as a function of hydrolysis of the phosphoester bond of the polymer upon degradation.

110. The method of claim 96 wherein said article is non-toxic and results in minimal tissue irritation when implanted or injected into vasculated tissue.

111. The method of claim 96 wherein said article is in the form of a laminate for degradable fabric.

112. The method of claim 96 wherein said polymer composition is used as a coating for an implant.

113. The method of claim 96 wherein the polymer composition is used as a barrier for adhesion prevention.

114. The method of claim 96 wherein said polymer composition is fabricated as a tube for nerve generation.

115. The biodegradable terephthalate polymer composition of claim 55, wherein said biologically active substance is an analgesic.

116. The biodegradable terephthalate polymer composition of claim 56, wherein said biologically active substance is an analgesic.

117. The biodegradable terephthalate polymer composition of claim 57, wherein said biologically active substance is an analgesic.

118. The biodegradable terephthalate polymer composition of claim 58, wherein said biologically active substance is an analgesic.

119. The biodegradable terephthalate polymer composition of claim 59, wherein said biologically active substance is an analgesic.

120. The biodegradable terephthalate polymer composition of claim 60, wherein said biologically active substance is an analgesic.

121. The biodegradable terephthalate polymer composition of claim 61, wherein said biologically active substance is an analgesic.

122. The biodegradable terephthalate polymer composition of claim 62, wherein said biologically active substance is an analgesic.

123. The biodegradable terephthalate polymer composition of claim 63, wherein said biologically active substance is an analgesic.

124. The biodegradable terephthalate polymer composition of claim 64, wherein said biologically active substance is an analgesic.

125. The biodegradable terephthalate polymer composition of claim 65, wherein said biologically active substance is an analgesic.

126. The biodegradable terephthalate polymer composition of claim 66, wherein said biologically active substance is an analgesic.

* * * * *